United States Patent
Barath

(10) Patent No.: US 7,837,670 B2
(45) Date of Patent: Nov. 23, 2010

(54) METHODS AND DEVICES FOR DELIVERING THERAPEUTIC AGENTS INTO THE PROSTATE GLAND

(75) Inventor: Peter Barath, Oakbrook, IL (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 11/087,073

(22) Filed: Mar. 22, 2005

(65) Prior Publication Data

US 2006/0217680 A1    Sep. 28, 2006

(51) Int. Cl.
*A61M 31/00* (2006.01)

(52) U.S. Cl. .................. 604/517; 604/514; 604/103.01

(58) Field of Classification Search ............... 604/523, 604/514, 517, 101.01, 103.01, 103.08, 507
See application file for complete search history.

(56) References Cited

U.S. PATENT DOCUMENTS

| | | | | |
|---|---|---|---|---|
| 3,977,408 A | | 8/1976 | MacKew | 128/349 B |
| 5,007,897 A | * | 4/1991 | Kalb et al. | 604/43 |
| 5,112,305 A | | 5/1992 | Barath et al. | 604/96 |
| 5,242,397 A | | 9/1993 | Barath et al. | 604/96 |
| 5,336,178 A | * | 8/1994 | Kaplan et al. | 604/509 |
| 5,419,763 A | | 5/1995 | Hildebrand | 604/54 |
| 5,681,281 A | | 10/1997 | Vigil et al. | 604/96 |
| 5,713,863 A | | 2/1998 | Vigil et al. | 604/104 |
| 5,746,716 A | | 5/1998 | Vigil et al. | 604/97 |
| 5,843,016 A | | 12/1998 | Lugnani et al. | 604/21 |
| 5,873,852 A | | 2/1999 | Vigil et al. | 604/52 |
| 6,102,904 A | | 8/2000 | Vigil et al. | 604/500 |
| 6,210,392 B1 | | 4/2001 | Vigil et al. | 604/507 |
| 6,547,803 B2 | * | 4/2003 | Seward et al. | 606/185 |
| 6,656,155 B2 | | 12/2003 | Freyman | 604/103.01 |
| 6,692,493 B2 | * | 2/2004 | McGovern et al. | 606/41 |
| 6,695,839 B2 | | 2/2004 | Sharkey | 606/49 |
| 2002/0162521 A1 | | 11/2002 | Shkolnikov et al. | 123/46 |
| 2003/0092689 A1 | * | 5/2003 | Escandon et al. | 514/171 |
| 2003/0114793 A1 | * | 6/2003 | Freyman | 604/103.1 |
| 2004/0002647 A1 | * | 1/2004 | Desai | 600/417 |
| 2004/0010301 A1 | | 1/2004 | Kindlein et al. | 607/101 |

(Continued)

FOREIGN PATENT DOCUMENTS

EP    0044804 A1    1/1982

(Continued)

OTHER PUBLICATIONS

G. Kerr Whitfield et al., "Steroid Hormone Receptors: Evolution, Ligands, and Molecular Basis of Biologic Function," *Journal of CellularBiochemistrySupplements*, 32/33 (1999): 110-122.

(Continued)

*Primary Examiner*—Nicholas D Lucchesi
*Assistant Examiner*—Laura A Bouchelle
(74) *Attorney, Agent, or Firm*—Mayer & Williams PC; David B. Bonham; Stuart H. Mayer

(57) ABSTRACT

The present invention is directed to the treatment of various ailments associated with the prostate gland, including benign prostate hypertrophy (BPH), cancer and chronic inflammatory diseases. The present invention describes, inter alia, devices, methods and therapeutic agents for the treatment of prostatic ailments.

30 Claims, 13 Drawing Sheets

U.S. PATENT DOCUMENTS

| | | | | |
|---|---|---|---|---|
| 2004/0024355 | A1* | 2/2004 | Tsukada | 604/101.01 |
| 2004/0064094 | A1 | 4/2004 | Freyman | 604/103.01 |
| 2004/0215181 | A1* | 10/2004 | Christopherson et al. | 606/32 |

FOREIGN PATENT DOCUMENTS

| | | |
|---|---|---|
| WO | WO 97/31611 | 9/1997 |
| WO | WO 97/36631 | 10/1997 |
| WO | WO 99/59666 | 11/1999 |
| WO | WO 03/033045 A2 | 4/2003 |
| WO | WO 03/051442 A2 | 6/2003 |

OTHER PUBLICATIONS

Yasuhiro Shibata et al., "Comparison of Histological Compositions and Apoptosis in Canine Spontaneous Benign Prostatic Hyperplasia Treated with Androgen Suppressive Agents Chlormadinone Acetate and Finasteride," *Journal of Urology*, 165 (2001): 289-293.

Ann W. Hsing et al., "Hormones and Prostate Cancer: Current Perspectives and Future Directions," *The Prostate*, 52 (2002): 213-235.

Christopher K. Glass et al., "The coregulator exchange in transcriptional functions of nuclear receptors," *Genes & Development*, 14 (2000): 121-141.

Natasha Kyprianou et al., "Activation of Programmed Cell Death in the Rat Ventral Prostate after Castration," *Endocrinology*, 122 (1988): 552-562.

Partha P. Banerjee et al., "Lobe-Specific Apoptotic Cell Death in Rat Prostate after Androgen Ablation by Castration," *Endocrinology*, 136 (1995): 4368-4376.

Kaitkanoke Sirinarumitr et al., "Finasteride-induced prostatic involution by apoptosis in dogs with benign prostatic hypertrophy," *Am.J. Vet. Res.*, 63 (2002): 495-498.

K. Suzuki et al., "Estimation of Canine Prostatic Volume: Nomogram Based on Prostatic Cubic Volume," *International Urology and Nephrology*, 30 (1998): 725-730.

D. Tavian et al., "Androgen receptor mRNA under-expression in poorly differentiated human hepatocellular carcinoma," *Histology and Histopathology*, 17 (2002): 1113-1119.

Gerald Sufrin et al., "A New Model for Studying the Effect of Drugs on Prostatic Growth 1. Antiandrogens and Dna Synthesis," 11 (1973): 45-54.

Nelson Stone, "Flutamide in Treatment of Benign Prostatic Hypertrophy," *Urology*, Supplement, 34 (1989): 64-68.

Arihiro Tomura et al., "The Subnuclear Three-dimensional Image Analysis of Androgen Receptor Fused to Green Fluorescence Protein," *Journal of Biological Chemistry*, 276 (2001): 28395-28401.

Manjunath S. Si-Let et al., "Metabolism of the antiandrogenic Drug (Flutamide) by Human CYP 1 A2," *Drug Metalbolism and Disposition*, 25 (1997): 1298-1303.

Zhong Zuo et al., "Flutamide-Hydroxypropyl-$\beta$-cyclodextrin Comples: Formulation, Physical Characterization, and Adsorption Studies using the Caco-2 in vitro Model," *J. Pharm. Pharmaceut. Sci*, 3 (2000): 220-227.

D.R. Greene et al., "Sonographic Measurements of Transition Zone of Prostate in Men with and without Benign Prostatic Hyperplasia," *Urology*, 36 (1990): 293-299.

Martha K. Terris et al., "Determination of Prostate Volume by Transrectal Ultrasound," *Journal of Urology*, 145 (1991): 984-987.

Hiroki Watanabe et al., "Measurements of Size and Weight of Prostate by Means of Transrectal Ultrasonotomography," *Tohoku J. Exp. Med*, 114 (1974): 277-285.

A.R. Zlotta et al., "The importance of measuring the prostatic transition zone: an anatomical and radiological study," *BJU International*, 84 (1999): 661-666.

Theodore L. Deweese et al., "A Phase I Trial of CV706, a Replication-competent, PSA Selective Oncolytic Adenovirus, for the Treatment of Locally Recurrent Prostate Cancer following Radiation Therapy," *Cancer Research*, 61 (2001): 7464-7472.

Louis L. Pisters et al., "Evidence That Transfer of Functional p53 Protein Results in Increased Apoptosis in Prostate Cancer," *Clinical Cancer Research*, 10 (2004): 2587-2593.

Martha K. Terris, "Ultrasonography and Biopsy of the Prostate," in *Campbell's Urology*, vol. 4 (Saunders: Philadelphia, 2002), pp. 3038-3054.

Mark Frydenberg et al., Benign Prostate Disorders, Chap. 9. Nov. 9, 2004. http://www.endotext.org/male/male9/male9.htm.

* cited by examiner

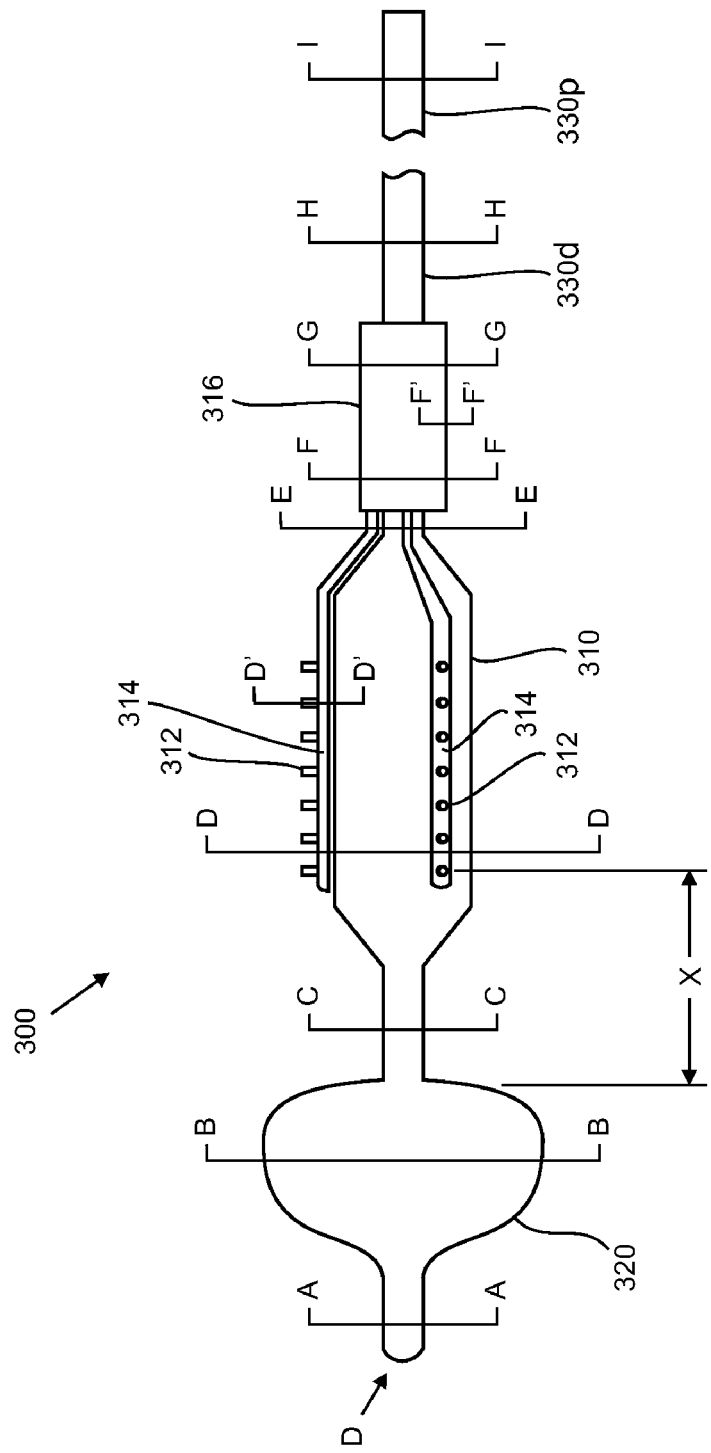

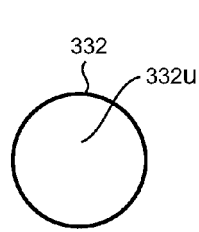
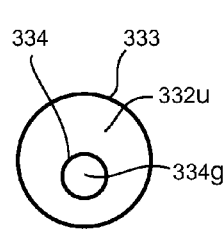
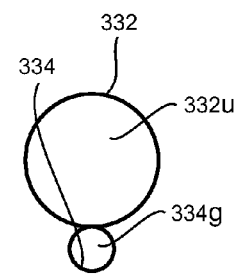
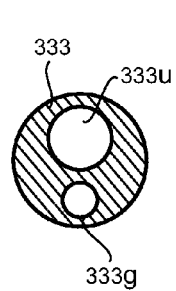
*FIG. 3A*  *FIG. 3A'*  *FIG. 3A"*  *FIG. 3A'''*
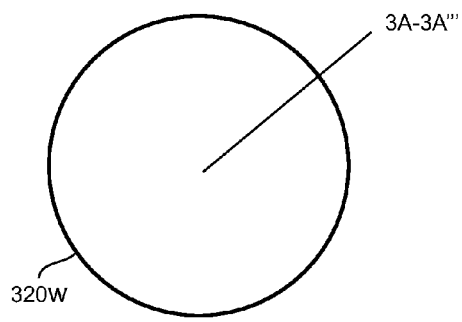
*FIG. 3B*
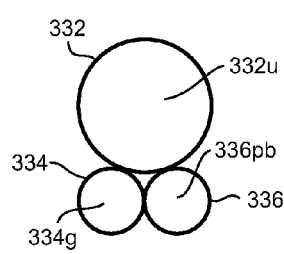
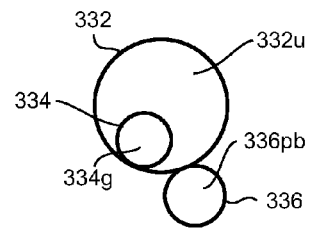
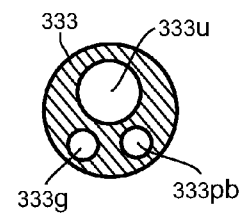
*FIG. 3C*  *FIG. 3C'*  *FIG. 3C"*

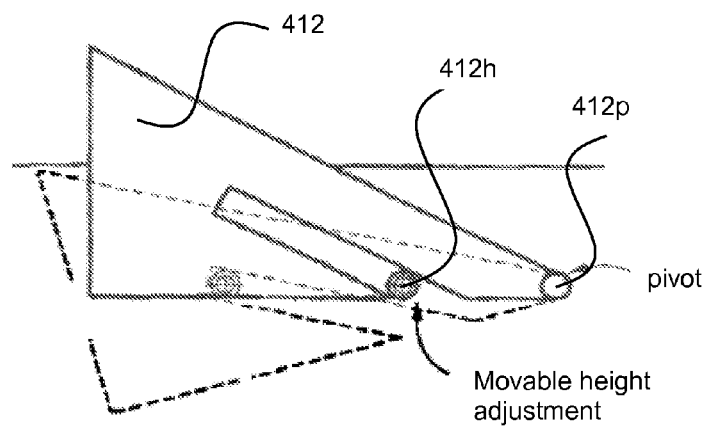
Fig. 4
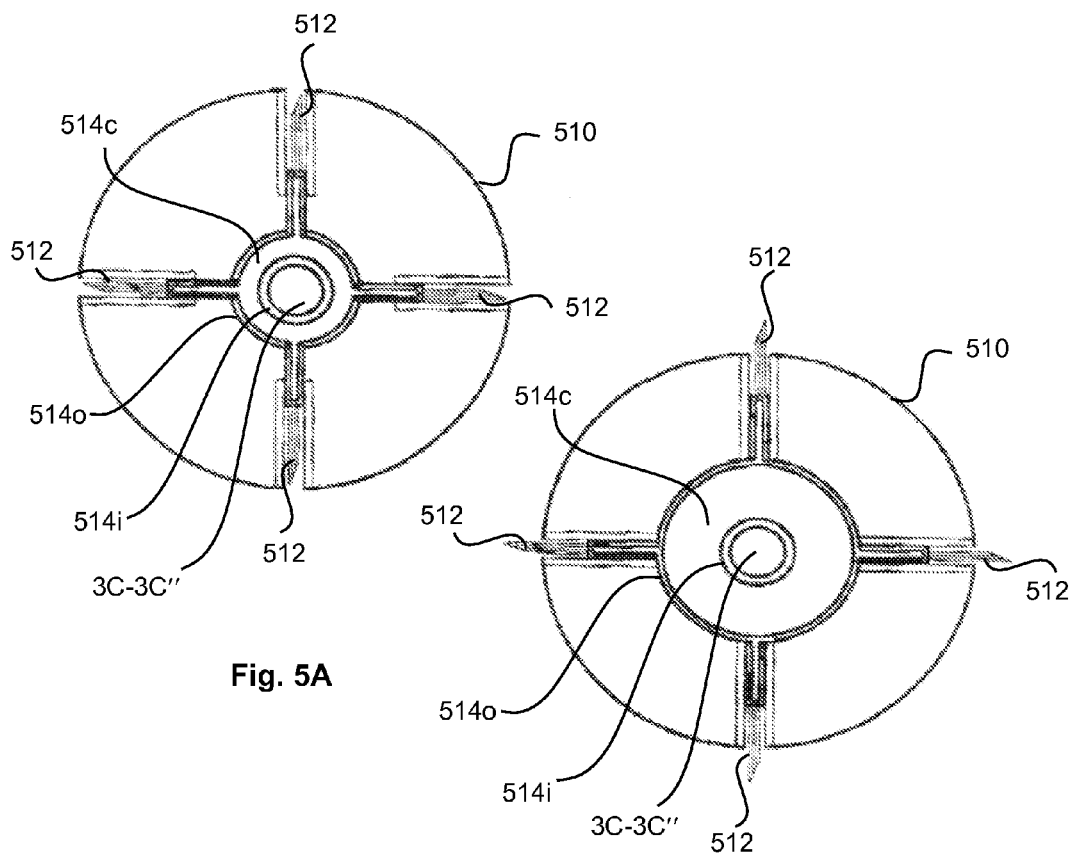
Fig. 5A
Fig. 5B

METHODS AND DEVICES FOR DELIVERING THERAPEUTIC AGENTS INTO THE PROSTATE GLAND

FIELD OF THE INVENTION

The field of art to which this invention relates is in the treatment of various diseases and conditions associated with the prostate gland, including benign prostate hypertrophy (BPH), cancer and chronic inflammatory diseases. The present invention describes, inter alia, devices, methods and therapeutic agents for the treatment of such prostatic ailments.

BACKGROUND OF THE INVENTION

With reference to FIGS. 1 and 2, which depict the male urogenital anatomy 10, the prostate 20 is a complex, walnut-sized gland in the male urogenital anatomy 10 that is located just below the bladder 22. The walls 23 of the bladder 22 relax and expand to store urine and contract and flatten to empty urine through the urethra 28, which extend from the bladder 23, through the prostate 20, and to the end of the penis 24.

The part of the urethra 28 that is surrounded by the prostate 20 is referred to as the prostatic segment of the urethra, or prostatic urethra. The prostate 20 also surrounds the ejaculatory ducts 25 where they enter the prostatic urethra 28. During sexual excitement, the sperm leave the epididymis 27 (which is attached to the surface of the testis) and is carried by the ductus deferens 29 in the direction of the prostate 20. A primary function of the prostate 20 is to supply nutritional fluid for the sperm to form semen during ejaculation. This fluid, which is produced in the seminal vesicles 21 (see FIG. 2) is added to the semen during ejaculation. On each side, the ductus deferens 29 and seminal vesicle 21 join to form a single tube called the ejaculatory duct 25. Each ejaculatory duct 25, left and right, carries the seminal vesicle secretion and sperm through the prostate gland 20, emptying into the prostatic urethra 28.

According to a typical model of the prostate, four different anatomical zones may be distinguished, which have anatomo-clinical correlation: (1) The peripheral zone 1, which is the area forming the postero-inferior aspect of the gland. It represents 70% of the prostatic volume, and is the zone where the majority (60-70%) of prostate cancers form. (2) The central zone 2, which represents 25% of the prostate volume and through which the ejaculatory ducts pass. This is the zone which usually gives rise to inflammatory processes (e.g., prostatitis). (3) The transitional zone 3, which represents only 5% of the total normal prostatic volume and is the zone where benign prostatic hypertrophy occurs. It consists of two lateral lobes together with periurethral glands. Approximately 25% of prostatic adenocarcinomas also occur in this zone. (4) The anterior zone 4, which is predominantly fibromuscular.

The prostate 20 weighs approximately 20 g by the age of 20 and has the shape of an inverted cone, with the base at the bladder neck and the apex at the urogenital diaphragm. The prostatic urethra 28 does not follow a straight line as it runs through the center of the prostate gland 20 but it is actually bent anteriorly near the point where the ejaculatory ducts joins the prostate.

A significant portion of the male populace sooner or later faces complaints related mostly, although not exclusively, to the increased size of the prostate gland, known as benign prostate hypertrophy ("BPH"). The predominant symptoms of BPH are an increase in frequency and urgency of urination, as well as retention of urine in the bladder, which eventually can lead to complete inability to urinate. The condition significantly alters the quality of life. Moreover, urinary retention inevitably leads to lower urinary tract infection ("LUTI"). The LUTI then ascends into the kidneys causing chronic pyelonephritis, which eventually leads to renal insufficiency and death, unless the cause (i.e., the BPH and its associated urine retention) is eliminated or at least abated. With the aging of the male population, this scenario is becoming more and more frequent.

BPH is the consequence of the disturbed balance between the continuous production and natural death (apoptosis) of the glandular cells of the prostate. Overwhelming cell production leads to increased prostate size and dislodgement/ engorgement of the urinary tract segment, which traverses the prostatic gland (i.e., prostatic urethra). The cause of the disturbed balance is thought to be the dihydrotestosterone (DHT), an enzymatically converted form of the male hormone, testosterone. This hormone is the dominant male hormone in the adult prostate. It forms a complex with the androgen receptors. The complex enters the nuclei of the cells, and maintains and extends cell proliferation and prevents apoptosis.

In mild cases of BPH, medical treatment can alleviate the symptoms for some period of time. For example, alpha-adrenergic blockers (e.g. Hytrin), which relax the smooth muscle cell components of the prostate, can be effective until the glandular elements become overwhelming in the organ. Moreover, the enzyme blocker, finasteride, which prevents DHT production, also alleviates the complaints in about half of the cases but only after 6 months of oral treatment.

Advanced cases of BPH, however, can only be treated by mechanical or physical interventions such as transurethral physical destruction of prostatic tissue, for example using mechanical fragmentation, heat, cryosurgery, congelation, and so forth. These interventions often give only transient relief, at the expense of significant peri-operative discomfort and morbidity. A common prostate surgery involves transurethral resection of the prostate (TURP), which is accomplished by resecting the prostatic tissues surrounding the urethra that cause obstruction. Unfortunately, although effective in reducing obstructions, the dominant mechanism behind TURP is the progressive coring-out of the prostate, beginning at the level of the urethra and progressing outward into the prostatic capsule. Hence, this surgical procedure is destructive to the urethra and carries various complications including urinary incontinence, retrograde ejaculation, and impotence. Moreover, there is a high recurrence rate.

Another treatment modality employed is the surgical removal of the prostate (prostatectomy). It is a more definite solution, but it is a major surgery, is often associated with high morbidity and fairly high mortality, and often leads to severe sexual dysfunction.

Prostate cancer is the leading cancer diagnosis and the second most common cancer-related cause of death in men in the USA. It is the fourth most common malignancy worldwide. There has been a dramatic increase in the annual incidence: from 2.3% between 1975 and 1985 to 14% between 1992 and 1995 (Surveillance, Epidemiology and End Result program of the National Cancer Institute). The mortality rate, however, has undergone a slight decrease since 1995.

Several techniques are currently practiced for the treatment of prostate cancer, including the following: (1) Radical (anatomic retropubic or perineal) prostatectomy, which is a major intervention with high morbidity (e.g., thromboembolic and bleeding complications, erectile dysfunction, etc.) and fairly high mortality. (2) Radiation therapy, for example, three dimensional conformal high energy beam radiation (neutron or proton), with or without intensity modulation. It is an expensive procedure, its effectiveness has not yet been proven in randomized studies, and the procedure often leads to urethral strictures. (3) Brachytherapy, which involves the delivery, via an elaborate transperineal insertion procedure, of radioisotope seeds deep into the prostate tissue under ultrasound or MRI guidance. It is a lengthy operation under anesthesia, with high complication rates. (4) Systemic androgen suppression, which is objected to by many, especially in early stages of the cancer, due to feminization and erectile dysfunction. (5) Therapy with (neo)adjuvant agents, many of which are either proteins or polynucleotides, and therefore cannot be applied systemically due to the body's degradation processes.

Since an effective cancer therapy requires a minimum of five years, disease-free survival, there simply is not enough experience to know the efficacy of many of the newest therapeutic modalities. Nonetheless, a number of disadvantages of the current treatment methods are known as indicated above.

Inflammatory disease of the prostate (prostatitis) is the most important disease of the prostate after BPH and cancer. It is the most common urologic diagnosis in men younger than 50 years and the third most common in men older than 50 years. Prostatitis results in around 2 million office visits per year in the USA, corresponding to 8% of the total urology office visits. This condition significantly interferes with the quality of life due to constant pain (prostodynia) and urethral discharge. Well selected antibiotic treatment can eradicate the acute bacterial infection in most of the cases. However, the success rate with chronic prostatitis ranges from 0% to 67%, very often with an associated 90-day treatment period and high recurrence rate. This is partially due to the relative isolation of the prostate gland from the circulation, both anatomically as well as pharmacokinetically (e.g., acidic antibiotics have difficulty penetrating the alkaline prostatic acini).

Hence, present medical treatments are insufficient, lengthy and/or expensive, and the search for more effective, less invasive methods having less discomfort, longer lasting results and less expense continues.

SUMMARY OF THE INVENTION

The present invention is directed to the treatment of various diseases associated with the prostate gland, including benign prostate hypertrophy (BPH), cancer and chronic inflammatory diseases. The present invention describes, inter alia, various devices, methods and therapeutic agents for the treatment of prostatic ailments.

For example, according to one aspect of the invention, a method for delivering a therapeutic agent into the prostate gland of a mammalian subject is provided. The method comprises the following steps: (a) advancing a delivery catheter, which comprises a tissue penetrating member, through the urethra of the subject until the tissue penetrating member is positioned in the prostatic segment of the urethra; (b) extending the tissue penetrating member through the urethral wall; (c) injecting the therapeutic agent into tissue of the prostate gland via the tissue penetrating member; and (d) removing the catheter from the subject.

According to another aspect of the invention, a method of treating a disease or condition of the prostate gland is provided. This method comprises administering to a subject (e.g., by injection into the tissue of the prostate gland, among other methods) a therapeutically effective amount of a composition that comprises a therapeutic agent, which is selected from one or more of the following: agents that selectively target prostatic epithelial cell production or apoptosis, agents that selectively target testosterone-DHT conversion levels within the prostate, agents affecting androgen receptor binding within the prostate, and cell-cycle inhibitors.

According to yet another aspect of the invention, a novel catheter for delivery of a therapeutic agent to a prostate gland of a mammalian subject is provided. The catheter comprises: (a) an elongate body having an axis, a distal end, and a proximal end, (b) an expandable drug delivery member disposed at a first axial position along the elongate body and configured for transurethral delivery of the therapeutic agent into the prostate gland, and (c) an expandable positioning member that is (i) disposed at a second axial position along the elongate body that is distal to the expandable drug delivery member and (ii) configured for expansion within the bladder of the subject. The axial distance between the first and second axial positions in this aspect of the present invention is such that, when the expandable positioning member is expanded in the subject's bladder, and when the catheter is pulled back to the point where the expandable positioning member engages the bladder outlet, the expandable drug delivery member is properly positioned within the prostatic urethra.

These and other aspects and advantages of the present invention will become immediately apparent to those of ordinary skill in the art upon reading the disclosure to follow.

BRIEF DESCRIPTION OF THE DRAWINGS

FIG. 3 is a schematic illustration of a drug delivery catheter, in accordance with an embodiment of the present invention.

FIGS. 3A to 3A''' illustrate four alternative cross sectional views, taken along line A-A of the catheter of FIG. 3, in accordance with various embodiments of the present invention.

FIG. 3B illustrates a cross sectional view, taken along line B-B of the catheter of FIG. 3, in accordance with an embodiment of the present invention.

FIGS. 3C to 3C'' illustrate three alternative cross sectional views, taken along line C-C of the catheter of FIG. 3, in accordance with various embodiments of the present invention.

FIG. 3D'' illustrates cross sectional view, taken along line D'-D' of the catheter of FIG. 3, in accordance with an embodiment of the present invention.

FIG. 3F' illustrates cross sectional view, taken along line F'-F' of the catheter of FIG. 3, in accordance with an embodiment of the present invention.

FIG. 4 is a schematic illustration of a penetrating member, in accordance with an embodiment of the present invention.

FIGS. 5A and 5B are schematic illustrations of a scheme for a hydraulic penetration, in accordance with an embodiment of the present invention.

DETAILED DESCRIPTION OF THE INVENTION

Figure 1:
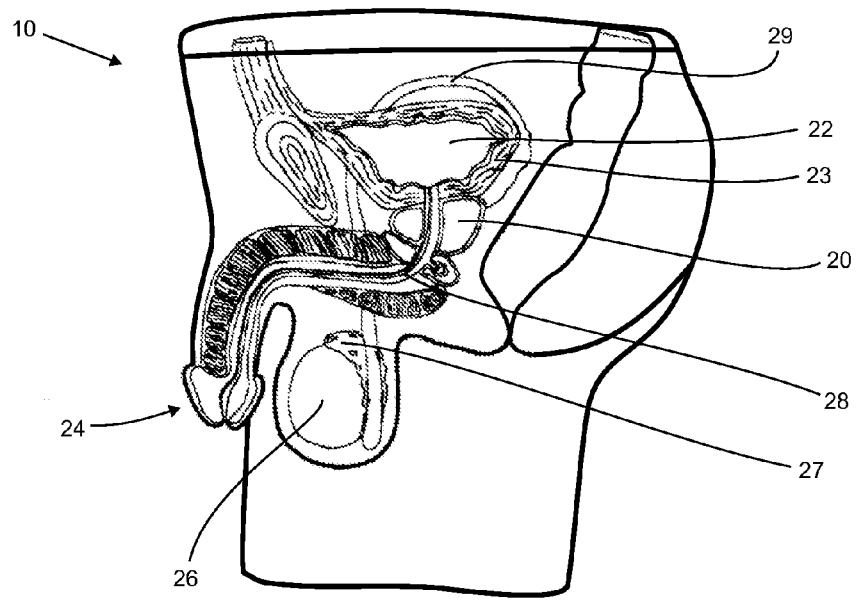
FIG. 1 is a schematic representation of the male urogenital anatomy.
Figure 2:
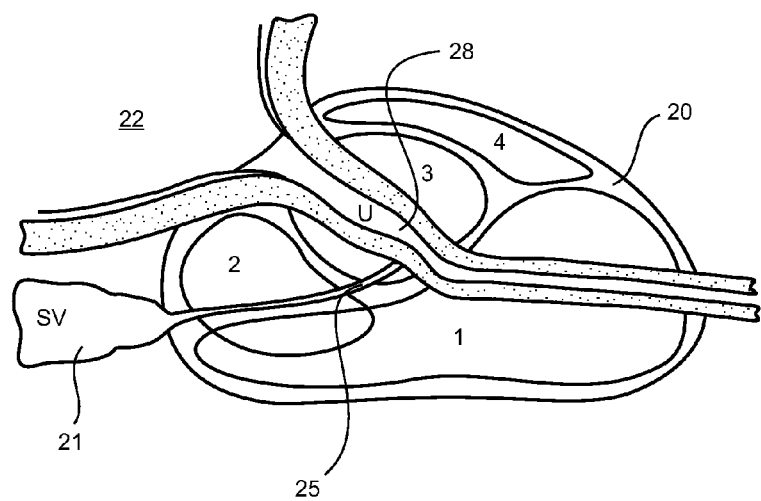
FIG. 2 is an enlarged schematic representation of prostatic area of the male urogenital anatomy.

The present invention now will be described more fully hereinafter with reference to the accompanying drawings, in which several embodiments of the present invention are shown. This invention may, however, be embodied in different forms and should not be construed as limited to the embodiments set forth herein. Furthermore, it is to be understood that the features of the various embodiments described herein can exist in various combinations and permutations.

In general, the present invention relates to methods and devices through which one or more therapeutic agents are injected into the prostate gland of a subject in connection with various treatments and to novel drug therapies for treatment of various ailments of the prostate. As used herein "therapeutic agents," "medicaments," "drugs," "pharmaceuticals" and other similar terms may be used interchangeably. Subjects are typically mammals, more typically humans and domesticated mammals such as horses and dogs.

According to a first aspect of the invention, a method of treating a disease or condition of the prostate gland (including treatment of BPH, malignant and benign tumors of the prostate, and inflammatory diseases of the prostate) is provided, which comprises administering one or more therapeutic agents to a subject. The therapeutic agents can be introduced using essentially delivery method, including oral, nasal, rectal, topical, bucal, parenteral, intradermal, intramuscular, transperineal, transurethral and transrectal methods, among others.

In certain embodiments, the therapeutic agents are directly introduced into the prostate. In these embodiments, any suitable device which can deliver a therapeutic composition directly into prostatic tissue may be employed, for example, by means of high or low pressure injection, spontaneous diffusion, facilitated diffusion (e.g., electrophoresis, iontophoresis), and so forth.

Diffusion, where employed, typically proceeds from the prostatic segment of the urethra into the prostatic tissue (i.e., transurethrally) to a point that is sufficiently deep to exercise the desired therapeutic effect. Injection, on the other hand, typically proceeds transurethrally, transperineally, or transrectally. A variety of devices are available in the medical arts for transurethral, transperineal, or transrectal delivery to the prostate. For example, various catheters are available which can be adapted for transurethral delivery, including porous balloon catheters, spiral diffusion catheters, and so forth. Various transurethral delivery catheters in accordance with the present invention are also described below.

For direct introduction, the therapeutic agent is typically provided in conjunction with a fluid formulation such as a gas (e.g., ozone), a liquid solution, a liquid dispersion (e.g., liquid formulations in which solid particles or liquid droplets are dispersed in a liquid phase, for instance, where the therapeutic agent is present within solid particles or within droplets that are dispersed in a liquid medium), or another gas or liquid formulation. Besides therapeutic agent, the fluid formulations will commonly contain a carrier fluid, for example, one or more inert gases for gaseous formulations, or water, organic solvent or a combination of the same for liquid formulations.

Administration can be single dose administration or in multiple dosages, separated by, for example, 1 day, 2 days, 4 days, 1 week, 2 weeks, 4 weeks, 8 weeks, 16 weeks, 6 months, one year or more.

Therapeutic agents that are administered (e.g., by indirect or direct delivery to the prostate) in conjunction with the present invention method are selected to target different cells and act via different mechanisms.

For example, apoptosis is a natural process and does not provoke significant tissue reaction, as opposed to agents with destructive characteristics (e.g., necrotizing and antitumor agents). Because BPH involves an imbalance between cell production and apoptosis, prime agents for the treatment of BPH are those that enhance apoptosis. The potential for selectivity and the lack of inflammation and scar formation following apoptotic cell death, make this approach attractive for the treatment of BPH. Moreover, it is noted that the line between malignancies and hyperplasia can be fairly blurred in term of apoptosis, as the regulation of prostate growth can generally be thought of as the result of competition between cell replication and cell death. Therefore, apoptosis enhancing agents also have a significant role in the treatment of cancer, although brachytherapy and antiandrogen drugs presently form the backbone of this approach.

Some specific examples in which hyperplastic or malignant epithelial cells are targeted in the treatment of BPH and prostate cancer follow.

With respect to apoptosis of hyperplastic or malignant epithelial cells, the tissue mass of the prostate can be decreased by depriving cells of the androgens necessary for their survival using direct androgen receptor blockers. For example, apoptosis of hyperplastic and malignant epithelial cells is enhanced in some embodiments of the invention by depriving cells of the androgens necessary for their survival, for example, by using direct androgen receptor blockers (e.g. flutamide, its active derivative 2-hydroxyflutamide, or bicalutamide) or by overwhelming the receptors with DHT. Apoptosis of hyperplastic and malignant epithelial cells is enhanced in other embodiments of the invention through the use of direct apoptosis enhancers such as TGF beta, caspases, TNFR1, Fas, Trpm-2, calmodulin, calcium dependent nucleases, and so forth. Phenoxodiol, along with other small molecule drugs (in contrast to biopolymers such as those discussed above), are signal transduction inhibitors, including TPK pathways, which can restore the balance between cell production and apoptosis and are therefore used in further embodiments of the invention to target a reduction in hyperplastic or malignant epithelial cells. 5-alpha reductase inhibitors are employed in still further embodiments of the invention to reduce the testosterone conversion into DHT and induce apoptosis in both epithelial and stromal cells. In yet other embodiments of the invention, androgen receptors (at any level) are altered. Examples include agents that are directed to the alteration of the chaparonin complex, agents directed to the prevention of post-translational modifications such as phosphorylation and glycolization, and agents targeting of proteosomes and dimerization. Other candidates for enhancing apoptosis include nascence oxygen, e.g., ozone or a low concentration injection of hydrogen peroxide.

Hyperplastic or malignant epithelial cells are also targeted in various embodiments of the invention using conventional cell proliferation inhibitors and other antitumor agents, including conventional chemotherapeutic agents acting at various levels of the cell cycle. Candidates include alkylating agents (e.g., cyclophosphamide, etc.), antimetabolites (e.g., methotrexate, 5-fluorouracil, cytosine arabinoside, 6-mercaptopurine), antimitotic agents (e.g., vinca alkaloids, paclitaxel, epidophyllotoxins), antibiotics (e.g. doxyrubicin, actinomycin D, bleomycins), enzymes (e.g., 1-asparaginase), platinum coordination complexes (e.g. cisplastin), among others. The cell cycle can also be influenced by newer, antibody-type agents such as cyclin antibodies.

In still other embodiments of the invention, radiation based techniques are used. For instance, androgen-bound radioisotopes such as soft beta emitters (e.g., $^3$H-testosterone) or radiolabeled direct androgen receptor blockers (e.g., $^3$H-flutamide) selectively destroy androgen receptors of hyperplastic or malignant cells. In embodiments involving advanced cancer, conventional radioisotopes such as those used for brachytherapy ($^{103}$Pd or $^{125}$I) are employed, where the goal is the destruction of the malignant epithelial or undifferentiated cells on the periphery of the gland. Another example is technetium-99m ($^{99m}$Tc), which is available, for instance, in sulfate colloid form, complexed with hexamethyl-propyleneamine oxime ($^{99m}$Tc HM-PAO complex), as well as other forms of $^{99m}$Tc profiting from its k electron radiation.

Selective epithelial cell targeting is also achieved in some embodiments of the invention by using antibodies and radioactive or otherwise modified nucleic acid precursors targeting various types of epithelial cells, for example, transitional cells and secretory/columnar cells, or by targeting basal/stem cells, the source of epithelial cells. Basal/stem cells are responsible for only about 10% of the total cell number, but attacking these cell types eliminates the source of the cell supply. Therapeutic agents for targeting these cells include antibodies against nuclear proliferation markers (e.g. PCNA, Ki-67, pp32). Antikeratinins against type 4,5,6 keratinin also attack these cells because of their high keratinin content. Transitional cells are attacked in certain embodiments of the invention using labeled or modified nucleic acid precursors, e.g., $^3$H-thymidine, iododeoxyuridine, bromodeoxyuridine because of their high nucleic acid turnover. Although secretory/columnar cells are the primary targets for apoptotic manipulation (see above), antibodies against their major components are also used to target these cells in certain embodiments of the invention. Examples include antikeratinin type 8, 18, 19, anti-PSA, anti-acid phosphatase.

In other embodiments, smooth muscle cells of the prostate are targeted. For example, smooth muscle cells can be targeted with long-acting alpha-adrenergic blockers or with antibodies specific to smooth muscle cells or one of their components (e.g. HHF35, which is specific to smooth muscle cell actin).

In further embodiments, all prostatic cells are indiscriminately targeted by using chemically or otherwise destructive agents, e.g. ethanol, fixatives, etc.

Certain additional embodiments of the invention for treatment of prostate cancer are directed to local delivery (e.g., via transurethral, transperineal, or transrectal delivery) of (neo) adjuvant therapies to the prostate. These therapeutic agents are prime drugs for use in conjunction with the present invention for the following reasons: (a) the need to avoid systemic side-effects arising from many of these agents (e.g., anti-androgens) and (b) the difficulties associated with systemic delivery of many of these agents, arising, for example, from the fact that (neo)adjuvant therapies are commonly based on administration of polypeptides and polynucleotides (e.g., proteins, antibodies, genes, vaccines, etc). The difficulty with the systemic administration of polypeptides, polynuclotides, and other biopolymers, is that they are enzymatically disintegrated and antibodies are formed against them. Various methods described in accordance with the present invention address these problems by supplying the medicaments directly to the targeted cells.

For example, in subjects with low-grade cancer, local delivery of anti-androgens in accordance with the present invention can be substituted for systemic androgen suppression, thereby reducing or eliminating hypophyseal rebound as well as systemic feminization.

Additional therapeutic agents for the treatment of prostate cancer in accordance with certain embodiments of the invention include the following: (a) cytokines including interleukins, interferons, chemokines, colony-stimulating factors and other factors including tumor necrosis factors, for example, Multikine™ (a mixture of interleukins, interferons and colony-stimulating factors), (b) monoclonal antibodies for specific targeting of special cell types, (c) vaccine therapies, which enhance antigen presentation by sensitizing dendritic cells to a prostate cancer antigen (e.g., the ubiquitous PSA), for example, Provenge™, and (d) gene therapies, for example, those using local adenoviral or liposomal transfection, e.g., INGN 201 (Ad-p53), a replication-defective adenoviral vector that encodes a wild-type p53 gene driven by the cytomegalovirus promoter (see, Pisters L L et al., "Evidence that transfer of functional p53 protein results in increased apoptosis in prostate cancer," *Clin. Cancer Res.* 2004 Apr. 15; 10(8):2587-93) and CV706, a PSA-selective, replication-competent adenovirus that has been shown to selectively kill human prostate cancer xenografts in preclinical models (see, DeWeese T L, et al., "A phase I trial of CV706, a replication-competent, PSA selective oncolytic adenovirus, for the treatment of locally recurrent prostate cancer following radiation therapy," *Cancer Res.* 2001 Oct. 15; 61(20):7464-72).

For prostatic infections, the responsible noxa (e.g., microbes, factors maintaining chronic and acute inflammation, etc.) are targeted with direct delivery of an antimicrobial agent and, in chronic infiltrative cases, steroidal agents.

Combinations of two or more drug approaches may also be employed. As a specific example, to the extent that inducing apoptosis in the androgen receptor containing cells is insufficient (e.g., due to the high turnover rate of the epithelial cells, which might replace the apoptotic cell mass), attacking the basal cells with keratin antibodies, PCNA, Ki-67, etc. to eradicate the source of this replacement may provide a longer lasting effect.

In certain embodiments of the invention, steroidal compounds, antimicrobial compounds, or both, are combined with other various cell targeting agents such as those discussed above. For example, steroidal agents may be desirable to address sterile inflammation issues, while antimicrobial compounds may be desirable to address infection issues (e.g., in the case of transurethral delivery, because the urethra is potentially a non-sterile environment). Sterilization of the urine with antimicrobial agents and swabbing the area with iodine may also be used to address this latter issue.

In accordance with another aspect of the present invention, the above and other prostatic drugs are delivered to the prostate of a subject by a method that comprises the following: (a) positioning a drug delivery catheter that contains at least one tissue penetrating member in the prostatic segment of the urethra of the subject, (b) extending the at least one tissue penetrating member until the distal end of the same pierces (i.e., traverses) the urethral wall, and (c) injecting the therapeutic agent into the prostate gland via the tissue penetrating member.

A typical catheter for the practice of the present invention includes a catheter shaft and a working member at or near the distal end of the shaft, which contains the tissue penetrating member(s). Where a plurality of tissue penetrating members are provided, they can be arranged along the working member in an organized fashion (e.g., in linear rows, in helical rows, in circular rows, and so forth) or in a more random pattern.

Once the catheter is placed at a desired location within the prostatic urethra, the working member is adapted to extend the tissue penetrating member(s) through the urethral wall, for example, by radially extending the tip of the penetrating member(s). This may be done, for example, by associating the penetrating member(s) with an expanding member, for instance, by placing the penetrating member(s) at or near the surface of a balloon, or on an expanding metallic or plastic frame.

In addition to piercing the urethral wall with the penetrating member(s), this step also serves to help immobilize the working member at the desired urethral position. It can also instantaneously improve urethral stricture, due to a dilatational effect associated with the expanding member, thereby providing relief from acute symptoms. Moreover, where a balloon is employed, the working member can establish tight continuous contact with the urethral wall, thereby helping prevent therapeutic agent from reentering the urethra via the various ducts of the prostate gland.

Examples of tissue penetrating members include needles, nipples, and other protuberances which are configured to allow the urethral wall to be pierced. Typically, the penetrating members are provided with a lumen through which therapeutic agent can be passed into the prostatic tissue.

In general, the length of the penetrating member is dictated by the depth of penetration that is desired. For example, as discussed above in connection with FIG. 1, the transitional zone, which is the zone where benign prostatic hypertrophy occurs, lies just beyond the wall of the prostatic urethra, indicating that, for the treatment of BPH, penetrating members may be used that are just long enough to penetrate the urethral wall.

The central zone, on the other hand, lies beyond the transition zone or beyond the urethral wall in the region adjacent to the bladder where the urethral wall is relatively thick, indicating that the use of relatively longer penetrating members may be beneficial in certain embodiments, as compared with the lengths desired for the treatment of BPH. (Although as seen from the Examples below, therapeutic agent dispensed from relatively short penetrating members, relative to the size of the prostate, has been shown to become widely distributed in the prostate.) The central zone is the zone that usually gives rise to inflammatory processes.

Some portions of the peripheral zone lie just beyond the wall of the prostatic urethra, while other portions of the peripheral zone lie beyond the transition zone, the central zone or both. As noted above, this is the zone where the majority (60-70%) of prostate cancers form. Thus, relatively short or relatively long penetrating members may be indicated, depending on the location of the cancer. (Although, again, as seen from the Examples below, therapeutic agent dispensed from relatively short penetrating members has been shown to become widely distributed in the prostate.)

Also, a deep penetrating member may be used to in an attempt to avoid close contact between a radiation source or toxic agent with the urethra, whose damage is the source of a high percentage of complications (obstruction, strictures) after brachytherapy. In this regard, a brachytherapy generally involves implantation of some 50 radioisotope seeds deep into the prostate using a transperineal approach under transrectal ultrasonographic or MRI guidance, and it is conducted in a surgical setting. With the present invention, however, brachytherapy may be performed with only a single injection of the radioisotope, for example, using deeply penetrating members.

In general, the length of the penetrating members ranges from 0.25 to 25 mm, although lengths outside this range are possible.

As noted above, the working member of the delivery catheter is typically disposed at or near the end of a shaft, which may contain one or more channels. Such channels can be used to facilitate the insertion of the device (e.g. a guide wire channel can be provided), to allow urine to bypass the catheter during the period of insertion, or for the operation of the device (e.g., channels can be provided for the inflation of one or more balloons or for the delivery of therapeutic agent). The shaft can also be provided with other features, such as electrical wires (e.g., to perform the expansion of the working member or to operate electrodes in the case where electrophoresis or iontophoresis is employed).

The proximal end of the catheter can be provided, for example, with inflation ports, delivery ports or other mechanical or electrical connectors, which can be attached, for example, to sources of inflation fluid, therapeutic agent, or electricity, for conveyance to the working member of the catheter.

In some embodiments, the catheter is provided with components or markers that assist in positioning the catheter at the proper location in the prostatic urethra using non-invasive imaging techniques, for example, ultrasonic imaging, fluoroscopic imaging, or magnetic resonance imaging (MRI), among others. In this regard, various materials are known from which such components or markers can be fabricated, which will increase the contrast between the components or markers and their surroundings when viewed using these imaging techniques, thereby assisting catheter placement.

For example, in x-ray based fluoroscopy, materials which are more absorptive of x-rays than the surrounding tissue (i.e., radiopaque materials such as metals, metal salts and oxides, particularly bismuth salts and oxides and iodinated compounds) are commonly used to enhance contrast. In ultrasonic imaging, materials are also available for increasing contrast, including various echogenic materials (i.e., materials that result in an increase in the reflected ultrasonic energy upon injection or insertion of the formulation) and echolucent materials (i.e., materials that result in a decrease in the reflected ultrasonic energy upon injection or insertion of the formulation). In MRI, contrast agents are commonly employed to increase imaging contrast, for example, agents containing elements that have a large magnetic moment with a relatively long electronic relaxation time, such as Gd(III), Mn(II) and Fe(III).

The catheter can also be positioned in the prostatic urethra without imaging guidance. For instance, in certain embodiments, the working member of the catheter is properly placed in the urethra using a positioning balloon. In this regard, the catheter can be provided with an inflatable balloon (also referred to herein as an intravesical balloon) distal to the working member to facilitate positioning of the working member in the prostatic segment of the urethra without image guidance, as discussed below.

With reference now to FIG. 3, illustrated therein is a delivery catheter 300 in accordance with an exemplary embodiment of the present invention. The catheter 300 includes a positioning balloon 320 near the distal end D of the catheter, which is ultimately inflated in the bladder of the subject and which is used to position the delivery balloon 310 without the need for image guidance. The catheter 300 also includes a drug delivery balloon 310, which is inflated in the prostatic urethra and from which therapeutic agent is injected into the prostate of the subject. The distance X between the delivery balloon 310 and the positioning balloon 320, can be varied as needed to correspond to subject anatomy and to target appropriate regions of the prostate gland.

At the surface of the delivery balloon 310 are provided a plurality of injectors 312 (fourteen illustrated, although the number can vary, two are individually numbered), which are arranged in groups on delivery strips 314 (seven injectors are provided on three delivery strips in this case, although the number of injectors and strips can clearly vary), which supply therapeutic agent to the injectors 312. The injectors 312 are provided in a linear arrangement here, but the arrangement geometry can also vary (e.g., random, spiral, circular, etc.). The length of the delivery balloon 310 can be varied from approximately equal to the spacing between the most proximal and distal injectors to substantially longer (as shown), with excess balloon being provided beyond the most distal and proximal injectors 312. The longer balloon 310 will provide more substantial sealing against the urethra during drug delivery until such time as the balloon 310 is deflated.

FIGS. 3A to 3A''' illustrate a few possible cross sections for the catheter of FIG. 3, taken along line A-A. The configuration of FIG. 3A is the simplest and includes a hollow urine shaft 332 forming a urine lumen 332u. As noted above, urine lumens are provided to allow urine to bypass the catheter during the period of insertion. The urine lumen optionally can extend through the positioning balloon to an opening at the distal end of the catheter. The opening is in fluid communication with the bladder where the catheter is inserted. The catheter, optionally, may include a coudé tip (not shown) at the distal end to facilitate insertion of the catheter through tortuous passages of the urethra (e.g., bulbar urethra).

FIGS. 3A' to 3A''' are more complex in that they include a guide wire lumen as well as a urine lumen. As noted above, guide wire lumens can facilitate the insertion of the devices of the invention. In FIG. 3A', a hollow guide wire shaft 334, which forms a guide wire lumen 334g, is provided within the urine lumen 332u of hollow urine shaft 332. Hollow urine and guide wire shafts 332, 334, are generally concentric and are free to move with respect to one another. FIG. 3A'' is similar to FIG. 3A', except that the guide wire shaft 334 and urine shaft 332 are adjacent (e.g., adhered to one another), rather than concentric. In FIG. 3A''', a guide wire lumen 333g and a urine lumen 333u are provided within an extruded body 333. Additional configurations are, of course, possible.

FIG. 3B is an illustration of the catheter of FIG. 3, taken along line B-B. This figure shows the wall 320w of the balloon of positioning catheter of FIG. 3. Within the wall 320w of FIG. 3B are typically provided a urine lumen and a guide wire lumen (not illustrated in FIG. 3B), corresponding, for example, to any of the various cross-sections described in FIGS. 3A to 3A''', among others.

FIGS. 3C to 3C'' illustrate a few exemplary cross sections for the catheter of FIG. 3, taken along line C-C. FIG. 3C illustrates the following, all joined together in an adjacent configuration: (a) a hollow urine shaft 332 defining a urine lumen 332u, (b) a hollow guide wire shaft 334 defining a guide wire lumen 334g, and (c) a hollow positioning balloon shaft 336 defining a positioning balloon lumen 336pb. FIG. 3C' illustrates a hollow urine shaft 332 defining a urine lumen 332u, within which is provided a hollow guide wire shaft 334 that defines a guide wire lumen 334g. A hollow positioning balloon shaft 336 defining a positioning balloon lumen 336pb is joined to the hollow urine shaft 332 in an adjacent configuration. In FIG. 3C'', a guide wire lumen 333g, a urine lumen 333u, and a positioning balloon lumen 333pb are provided within an extruded body 333. Additional configurations, including combinations of these configurations are possible. For example, an extruded body containing urine and guide wire lumens can be joined to a hollow positioning balloon shaft (not shown), and so forth. Hence, although FIG. 3C'' (as well as subsequent figures in this series) illustrate an extruded body 333 with various lumens formed therein, it should be realized that various other configurations are possible.

Figure 3D:
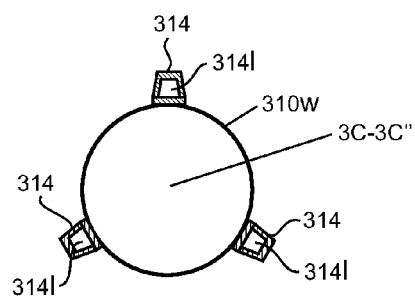
FIG. 3D illustrates a cross sectional view, taken along line D-D of the catheter of FIG. 3, in accordance with an embodiment of the present invention.
Figure 3D:
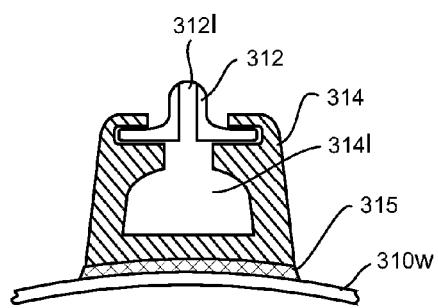

FIG. 3D illustrates an exemplary cross section of the catheter of FIG. 3, taken along line D-D. Shown in this figure are the wall 310w of the delivery balloon 310 of FIG. 3 as well as hollow delivery strips 314, each of which forms a drug delivery lumen 314l, through which therapeutic agent is conveyed to the subject. Within the delivery balloon 310 of FIG. 3D are typically provided a urine lumen, a guide wire lumen and a hollow positioning balloon lumen (not illustrated in FIG. 3D), corresponding, for example, to any of the various cross-sections described in FIGS. 3C to 3C''', among others.

FIG. 3D' illustrates an exemplary cross section of the catheter of FIG. 3, taken along line D'-D'. Shown in this figure is the wall 310w of the delivery balloon 310 of FIG. 3 to which is attached a delivery strip 314 (having a delivery strip lumen 314l) via an adhering material 315, such as an adhesive. Also provided at the particular cross-section selected for FIG. 3D' is an injector 312 which contains an injector lumen 312l. Upon inflation of the delivery balloon 310, the injector 312 penetrates the urethral wall (not shown), whereupon therapeutic agent is conveyed through the injector lumen 314l and into the prostate tissue.

Figure 3E:
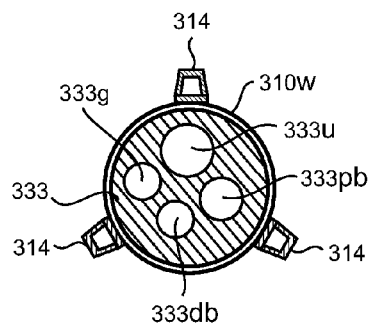
FIG. 3E illustrates cross sectional view, taken along line E-E of the catheter of FIG. 3, in accordance with an embodiment of the present invention.

FIG. 3E is an exemplary cross section of the catheter of FIG. 3, taken along line E-E, and shows three hollow delivery strips 314, attached to the surface of the wall 310w of the delivery balloon at the neck of the delivery balloon (see FIG.

3). Also illustrated in FIG. 3E is a cross-sectional view of an extruded body 333, which forms a guide wire lumen 333g, a urine lumen 333u, a positioning balloon lumen 333pb and a delivery balloon lumen 333db.

Figure 3F:
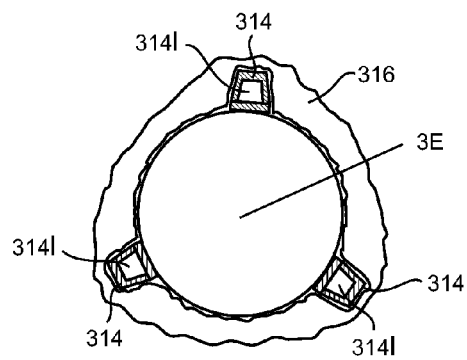
FIG. 3F illustrates a cross sectional view, taken along line F-F of the catheter of FIG. 3, in accordance with an embodiment of the present invention.
Figure 3F:
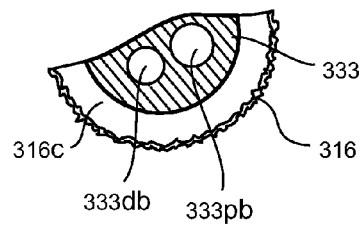

FIGS. 3F, 3F' and 3G are three cross-sections, taken along line F-F, line F'-F' and line G-G, respectively, within the region of the sleeve 316 of the catheter 300 of FIG. 3.

With reference to FIG. 3F, this figure shows three hollow delivery strips 314, having delivery strip lumens 314l, which are attached at an outer surface of a multi-lumen region. For example, the hollow delivery strips 314 can be attached to the outer surface of an extruded body, such as the extruded body 333 of FIG. 3E, among others. A sleeve 316 is also provided in FIG. 3F, for example, by adhering (e.g., by melt bonding) it to the hollow delivery strips 314 and the underlying multi-lumen region.

Figure 3G:
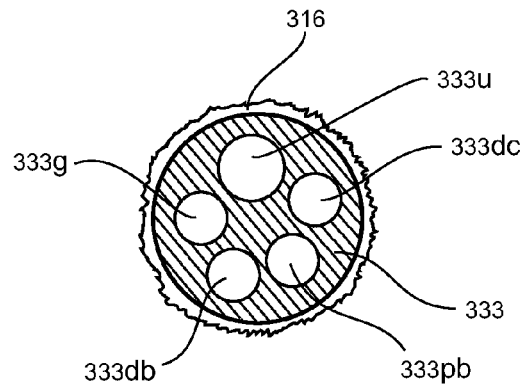
FIG. 3G illustrates a cross sectional view, taken along line G-G of the catheter of FIG. 3, in accordance with an embodiment of the present invention.

In FIG. 3G, which is proximal to FIG. 3F, drug is not conveyed within hollow delivery strips, but rather is conveyed within a drug circuit lumen 333dc. In this instance, the drug circuit lumen 333dc is formed in extruded body 333, along with a guide wire lumen 333g, a urine lumen 333u, a positioning balloon lumen 333pb and a delivery balloon lumen 333db. As in FIG. 3F, the sleeve 316 is adhered (e.g., by melt bonding) to the underlying multi-lumen region (extruded body 333).

In FIG. 3F', which lies between FIG. 3F and FIG. 3G, the sleeve 316 is not bonded onto the underlying multi-lumen region (extruded body 333). As a result, a channel 316c is created between the sleeve 316 and the underlying extruded body 333, which acts as a transition channel between the hollow delivery strips 314 of FIG. 3F and the drug circuit lumen 333dc of FIG. 3G (which extends to the surface of the extruded body at some point between line F'-F' and line G-G in FIG. 3, thereby introducing drug into the channel 316c).

Figure 3H:
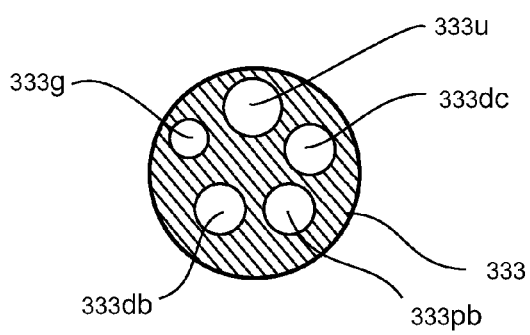
FIGS. 3H and 3H' illustrate two alternative cross sectional views, taken along line H-H of the catheter of FIG. 3, in accordance with two embodiments of the present invention.
Figure 3H:
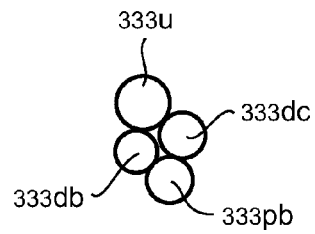

FIG. 3H is an exemplary cross section of the catheter of FIG. 3, taken along line H-H. FIG. 3H is similar to FIG. 3G in that is includes an extruded body 333 containing a guide wire lumen 333g, a urine lumen 333u, a positioning balloon lumen 333pb, a delivery balloon lumen 333db and a drug circuit lumen 333dc. FIG. 3H, however, does not include sleeve 316.

FIG. 3H' is an alternative adjacent-lumen design in which the following lumens are illustrated: a urine lumen 333u, a positioning balloon lumen 333pb, a delivery balloon lumen 333db and a drug circuit lumen 333dc. In contrast to FIG. 3H, during operation the guide wire is manipulated within the urine lumen of the design of FIG. 3H'. Hence no separate guide wire lumen is necessary for the catheter design of FIG. 3H'.

Figure 3I:
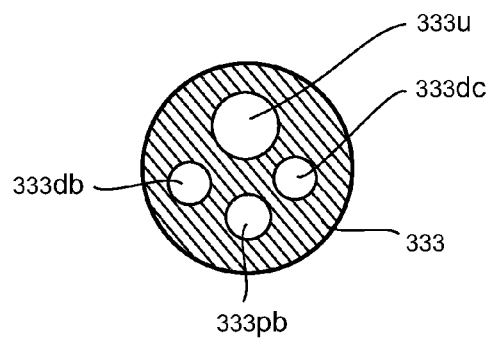
FIG. 3I illustrates a cross sectional view, taken along line I-I of the catheter of FIG. 3, in accordance with an embodiment of the present invention.

FIG. 3I is an exemplary cross section of the catheter of FIG. 3, taken along line I-I. FIG. 3I is similar to FIG. 3H in that is includes an extruded body 333 containing a urine lumen 333u, a positioning balloon lumen 333pb, a delivery balloon lumen 333db and a drug circuit lumen 333dc. The catheter of FIG. 3, however, does not include a guide wire lumen 333g at its proximal end as it is of a rapid exchange design in this particular embodiment.

Of course, innumerable variations on the above catheter design are possible. For example, the positioning balloon, positioning balloon lumen and guide wire lumen in the above illustrations can be removed without destroying the ability of the device to function as a drug delivery device, albeit with the need for image guidance or some other type of positioning mechanism.

As another example, the design of the injector 312 illustrated in FIG. 3D' is a fixed height design, whereas FIG. 4, on the other hand, illustrates an injector 412 having a movable pivot 412p and a movable height adjustment mechanism 412h, which allows the height to the injector 412 to be adjusted. The injector 412 of FIG. 4 is a retractable angulated protrusion, which penetrates the urethral wall automatically upon engagement with the urethral wall and with further advancement of the catheter. The design of the injector 312 illustrated in FIG. 3D', on the other hand, relies on the balloon inflation pressure to pierce the urethral wall.

As yet another example, the injectors 512 in the device of FIGS. 5A and 5B are extended beyond the surface of the balloon 510 during use. In particular, the outer wall 514o of injection fluid conduit 514c is elastic (while the inner wall 514i is rigid). As a result, the force associated with the injection of the drug-containing fluid into the injection lumen 514c acts to radially extend the injectors 512 beyond the surface of the balloon 510, as seen by comparing FIG. 5A with FIG. 5B. A urine lumen, a guide wire lumen, and a positioning balloon lumen (not illustrated), corresponding, for example, to any of the various cross-sections described in FIGS. 3C to 3C'', among others, can be provided within the inner wall 514i, as desired.

Once an appropriate catheter (e.g., one selected from the various catheter designs described herein above, or a catheter of another design which contains at least one tissue penetrating member) is obtained, the catheter is inserted into the subject's urethra and advanced, either with our without image guidance, to the prostatic segment of the urethra. After the proper position is reached, the at least one tissue penetrating member is extended until the distal end pierces (i.e., traverses) the urethral wall, whereupon a therapeutic-agent-containing composition (e.g., a liquid or a gaseous formulation) is injected into the tissue of the prostate gland.

For example, let it be assumed that the subject upon which the medical procedure is to be performed has a condition for which injection of a therapeutic agent into the prostate is indicated, for instance, BPH, prostate cancer, or prostatitis. Typically the drug delivery catheter would be supplied by the manufacturer in its most contracted position to provide the lowest possible profile in terms of diameter at the time of insertion. Appropriate time and/or temperatures are typically allowed for the prepping, equilibrating, processing, and loading of the therapeutic agent into the delivery catheter.

In certain embodiments, the insertion and advancement of the catheter are facilitated by the use of a guide wire, over which the catheter is subsequently advanced. These embodiments typically employ a delivery catheter having an over-the-wire or rapid exchange design. In these embodiments, the guide wire can be positioned as follows: First, a lubricated nasogastric tube, a ureteral catheter, or another suitable catheter, typically in the range of 4 F to 6 F, is inserted into the bladder though the urethra. The correct position of the tube can be verified by the presence of urine. A guide wire (typically on the order of 0.014" in diameter) is then inserted through the tube/catheter, and advanced until a generous loop of the wire is positioned in the bladder. The tube/catheter is then retracted while keeping the guide wire within the bladder. At this point an over-the-wire or rapid exchange delivery catheter is inserted over the guide wire and the working member is advanced to the prostatic urethra.

In some embodiments of the invention, the working member is advanced to the prostatic urethra using visual or image guidance, using, for example, fluoroscopy, ultrasonography, urethroscopy, MRI, and so forth. It may be desirable in some of these embodiments to provide the catheter with positioning features. For example, the working member of the catheter can be provided with components or markers which improve fluoroscopic, ultrasonic or MRI contrast, as discussed in more detail above. In some embodiments, the catheter is inserted without visual or image guidance. For example, the working member of the catheter can be positioned with the assistance of a distal positioning balloon such as that described above, or some other type of positioning mechanism.

Once the catheter is established at the desired position in the urethra, the at least one tissue penetrating member of the catheter is extended until the end of the tissue penetrating member pierces (i.e., traverses) the urethral wall, thereby placing it in contact with prostatic tissue. For example, as discussed above, the at least one penetrating member can be disposed on the outer surface of a balloon or other expanding member. In the case of a balloon, the balloon can then be inflated to a nominal working pressure sufficient to overcome urethral strictures, which is dependent upon the nature of the device (e.g., number and type of penetrating members, etc.). Typically, nominal working pressures that are sufficient to overcome urethral strictures range from 0.5 to 10 atmospheres. Expansion of the expanding member also prevents the catheter from changing its axial position in the urethra. Moreover, where a balloon is employed, tight continuous contact with the urethral wall is established, thereby helping prevent the therapeutic agent from reentering the urethra via the various ducts of the prostate gland. Expansion can also lead to a dilatory effect on the urethra, providing some relief vis-à-vis obstructive tissue in combination with the therapeutic effect of the agent.

Subsequent to penetration by the at least one penetrating member, a therapeutic-agent-containing composition is injected into the tissue of the prostate gland. This can be done in a variety of ways. For instance, a predetermined volume of therapeutic-agent containing fluid can be dispensed from the at least one penetrating member into prostatic tissue by simply using a syringe and applying an appropriate force (e.g., by hand or by means of an injector device).

In certain beneficial embodiments of the invention, the volume of the therapeutic-agent-containing composition to be delivered to the prostate is based on the estimated volume of the prostate. For example, in some embodiments, the volume of the therapeutic-agent-containing composition typically ranges from 5-50%, and more typically about 15-35%, of the calculated volume of the prostate.

Prostatic volume may be calculated, for example, using pre-procedural, ultrasonographic measurement. For instance, the literature describes transrectal ultrasound (TRUS) as a technique for determination of prostate volume both in dogs (Shibata et al, "Comparison of histological composition and apoptosis in canine spontaneous benign prostatic hyperplasia treated with androgen suppressive agents chlormadinone acetate and finasteride." *J. Urol.* 165:289, 2001) and in humans (see H. Watanabe et al., "Measurement of size and weight of prostate by means of transrectal ultrasonotomography," *Tohuku J. Exp. Med.* 114:277-285, 1974). TRUS is also an attractive method for positioning of the catheter within the prostatic segment of the urethra and can be performed in a urology office setting.

Using TRUS, various prostate dimensions can be measured including the following: the width (W), the antero-posterior (AP) dimensions in the transverse/axial view, and the length (L) and height (H) in the longitudinal/sagittal view. The prostate volume can be estimated, for example, using formulas such as those that follow.

Assuming an elliptical/football shape of the prostate (see Terris M K: "Ultrasonography and biopsy of the prostate." In: Campbell's Urology vol. 4 pp. 3038-3054. Saunders, Philadelphia, 2002), then the formula for the volume of the prostate is caculated as follows:

1.) $\Pi \div 6 \times W \times AP \times L$
2.) $8 \times (\text{surface area})^2 \div 3 \Pi \times W$ where the surface area is outlined with the cursor in the widest axial view, and W is the width at the widest axial view. Assuming prostate is of spheroid/egg shape to eliminate the less accurate L measurement (see Terris M K, Stamey T A: "Determination of prostatic volume by transrectal ultrasound." *J Urol* 145:984-989, 1991), then the formulas for the volume of the prostate are as follows:

1.) $\Pi \div 6 \times W^2 \times AP$ (for prostate <80 g~prolate spheroid)
2.) $\Pi \div 6 \times W^3$ (for prostate >80 g~spherical)

Other formulas for the volume of the prostate, presented in a 2002 slide presentation by Patel et al, are as follows:

1.) $H \times W \times L \times 0.52$
2.) $0.52 \times W^3$

Of course additional formulas can be developed, or prostate volume can be empirically correlated with various TRUS measured parameters. The prostate tissue specific gravity is reported to be 1.050 (see H. Watanabe et al., "Measurement of size and weight of prostate by means of transrectal ultrasonotomography," *Tohuku J. Exp. Med.* 114:277-285, 1974), therefore the weight can be calculated from the volume in $cm^3$.

Once a predetermined time has passed after therapeutic agent delivery (e.g., anywhere from 10 seconds to 1 hour, more typically 15 seconds to 5 minutes), the one or more penetrating members (and any associated expansion member) are pulled back from an expanded position to a contracted position, and the catheter is removed from the subject, along with the guide wire, if any, completing the procedure.

Figure 6A:
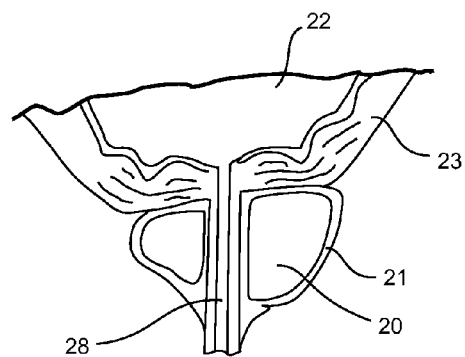
FIGS. 6A-6D illustrate a process for treating the prostate with a drug delivery device, in accordance with an aspect of the present invention.
Figure 6B:
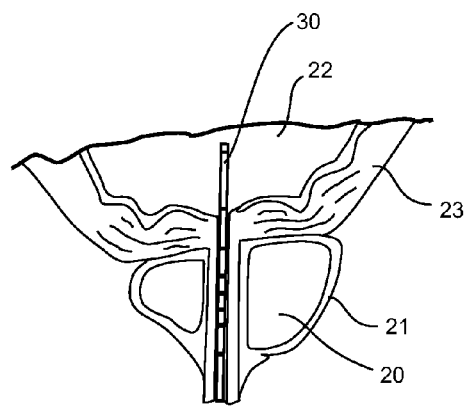
Figure 6C:
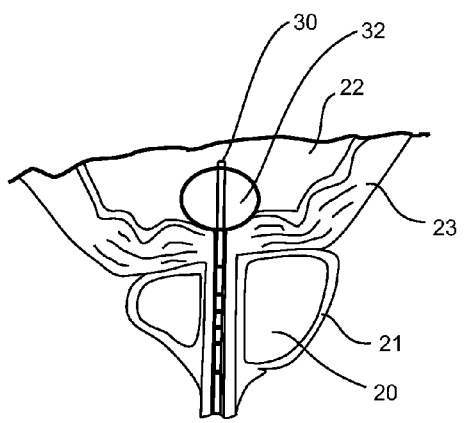
Figure 6D:
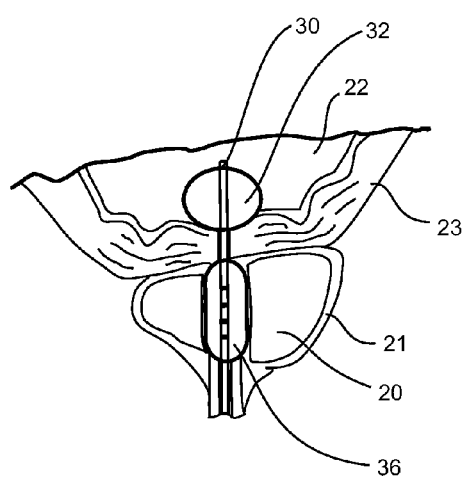

The operation of a catheter having a delivery balloon and a distal positioning balloon will now be described with reference to FIGS. 6A-6D, in accordance with an embodiment of the present invention. Referring now to FIG. 6A, a portion of the male urogenital anatomy is illustrated, with bladder 22, bladder wall 23, urethra 28 and prostate 20 (along with its capsular membrane 21) being shown. As a first step, a catheter 30 (e.g., a catheter like that described above) is delivered under local or lumbar anesthesia, retrograde through the penis, until the distal tip of the catheter is positioned in the bladder 22 as illustrated in FIG. 6B. This procedure can be conducted without fluoroscopic or other imaging assistance (e.g., ultrasonography) at the bedside. Knowledge that the distal end of the catheter is positioned in the bladder is typically confirmed by retrieval of urine. Subsequently, the positioning balloon 32 is inflated within the bladder 22. The catheter is then pulled back against the bladder outlet as illustrated in FIG. 6C, thereby providing the delivery balloon at a desired urethral location, based on the distance between the positioning balloon 32 and delivery balloon 36. Then, as illustrated in FIG. 6D, the delivery balloon 36 is inflated, whereupon penetrating members at the balloon 36 surface (e.g., injectors such as those described above, not shown) pierce the urethral wall. Drug is then injected through apertures in the penetrating members (e.g., injector lumens such as those described above) and into the tissue of the prostate 20.

In certain further aspects of the invention, the drug delivery device is provided with the capability to apply electrical current in order to enhance the delivery of the therapeutic agent. In these embodiments, the drug delivery device is typically provided with an electric charge of appropriate polarity, which will tend to drive the therapeutic agent through iontophoresis or electroporation.

As used herein, the term "iontophoresis" means the migration of ionizable molecules through a medium driven by an applied low-level electrical potential. This electrically mediated movement of molecules into tissues is superimposed upon concentration-gradient-dependent diffusion processes. If the medium or tissue through which the molecules travel also carries a charge, some electro-osmotic flow will occur. However, the rate of migration of molecules with a net negative charge towards the positive electrode, and vice versa, is generally determined by the net charge on the moving molecules and the applied electrical potential. The driving force may also be considered as electrostatic repulsion. Iontophoresis usually requires relatively low constant DC current in the range of from about 2-10 mA. In a well established application of iontophoresis, that of enhancing drug delivery through the skin (transdermal iontophoresis), one electrode is positioned over the treatment area and the second electrode is located at a remote site, usually somewhere else on the skin. In the present invention, the return electrode may be similarly positioned on the skin. Alternatively an electrode emerging from the distal end of the drug delivery device may serve as the return electrode. This method is particularly attractive in delivering antibiotics, where significant difficulties are associated with the delivery of antibiotics with acidic pH into the negatively charged prostate glandular system. Iontophoretically enhanced delivery requires that the therapeutic agent carry a net charge under physiological conditions.

As used herein, the term "electroporation" means the temporary creation of holes or pores in the surface of a cell membrane by an applied electrical potential and through which therapeutic agents may pass into the cell. Electroporation is now widely used in biology, particularly for transfection, where plasmids, DNA fragments, and other polynucleotide-containing materials are introduced into living cells. During electroporation pulsing, molecules that are not normally membrane-permeable are able to pass from the extracellular environment into the cells, due to a period of induced reversible membrane permeability. The permeable state is caused by the generation of an electrical field in the tissue which is of sufficient field strength to perturb the cell surface membrane's proteolipid structure. Unlike iontophoresis, electroporation can be used to enhance delivery of therapeutic agents that do not have a net charge into tissues.

Because these aspects of the present invention involve the use of electrical energy, there are many waveforms possible for use. Some examples of wave forms include square/rectangular waves, saw toothed waves, sinusoidal waves that do not reverse polarity, rectified sinusoidal waves, and modified versions of the same. The primary characteristic of the waveforms is that they provide a net flow of current to the working member located at the desired site in the prostate segment. It is to be appreciated by those skilled in the art that the waveforms must be capable of delivering the desired current under the varying impedances that are encountered in the working member and the surrounding vessel wall and fluids.

EXAMPLE 1

Dogs are subjected to anesthesia and are immobilized in supine position on a radiological table. A lubricated pediatric nasogastric tube (NGT) or a lubricated human ureter catheter (UC) is then inserted into the bladder through the penis. The bladder is visualized by injecting 10 ml of diluted contrast media under fluoroscopic control through the tube/catheter. A 0.014" coronary guide wire is then inserted forming a generous loop within the bladder. The UC is more suitable than the NGT for this purpose because of its opening at the end. The UC/NGT is then removed, keeping the guide wire in place. The opacified bladder serves as an anatomical guidance for localizing the prostate. The bladder neck, the sphincter, the intraprostatic as well as the distal segments of the urethra are identified by the anterograde flow of the contrast media along the guide wire. Catheters, either 7 or 8 mm diameter×15 mm long ((Boston Scientific/IVT (Interventional Technologies), San Diego, Calif., USA) are selected according to the dog size and/or to the estimated urethra size. The catheters are designed for transurethral delivery of a therapeutic agent into the prostate via urethral wall penetrating members. They are comprised of a balloon system with 21 penetrating members disposed on the outer surface of the balloon, a fluid delivery system in fluid connection with the penetrating members, and a member that the guide wire is inserted through. The penetrating members are arranged in 3 rows of 7 penetrating members, each row is disposed longitudinally on the outer surface of the balloon, with a radial orientation of 120 degrees between each row.

The catheter is inserted over the guide wire into the prostatic segment of the urethra using two radiopaque markers present on the device for orientation. The catheter can also be introduced without difficulty in the absence of a guide wire. Moreover, rather than fluoroscopy, in some cases transabdominal or transrectal ultrasound can be used to position the catheter. For example, in some cases, the device can be positioned within the prostatic segment of the urethra primarily using a transrectal ultrasound (TRUS) probe. After positioning the catheter by TRUS, the position can be cross-verified with fluoroscopy, using the contrast-filled bladder as anatomical guide.

After positioning the catheter, the balloon is inflated to 2 atm with undiluted contrast media. Either 150 uCi 3H-flutamide (0.15 ml in 5.0 ml normal saline) or 100 uCi 3H-testosterone (0.1 ml in 5.0 ml normal saline) both from Sigma, is injected into the prostate by hand injection, using a syringe in fluid communication with the penetration members. The balloon inflation is maintained for 30 seconds before the balloon is deflated, in order to minimize potential reflow from the prostate, and the catheter is then withdrawn. The total procedure time is about 5-7 minutes from anesthesia to removal of the catheter. The animals (2/time group) are sacrificed 1, 6, 12, 24 and 48 hours after the intervention.

The prostates are removed from a suprapubic incision, cleaned from the surrounding connective tissue, and immersed in 10% buffered formaldehyde. Samples are also taken from the seminal ducts, seminal vesicles, testicles, epididymis and liver. For autoradiography, the tissue samples are embedded in paraffin. Five-micron thick sections are cut, the sections are deparaffinized and covered with Ilford L4 nuclear emulsion. After 14 days exposure, they are developed in D19 developer and counterstained with eosin to visualize the structures but avoid the potential obscuring effect of hematoxyline on the nuclear binding of the label.

Results are provided in Table 1 and Table 2 below:

TABLE 1

Results of the tritium labeled testosterone

| Time | Information obtained from the experiments |
| --- | --- |
| 12 hours | Strong, selective glandular (but not stromal or muscular) nuclear activity in diffuse distribution over the whole prostate extending from the periurethral area to the periphery of the gland. Practically no free (extra-nuclear) activity. |
| 48 hours | Still strong, although somewhat less activity over the glandular nuclei; the distribution of the activity still covers the whole prostate, minimal scattered extra-nuclear labeling. |

TABLE 1-continued

Results of the tritium labeled testosterone

Figure 7:
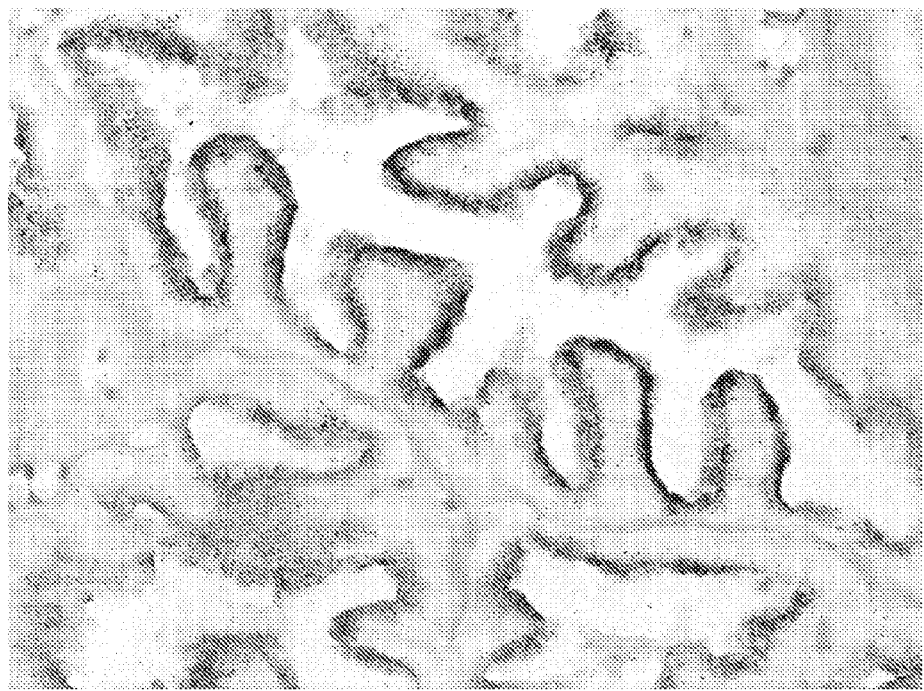
FIG. 7 is an autoradiographic picture of a hyperplastic prostate 48 hours after transurethral injection of 100 uCi of tritiated testosterone. Eosin counterstaining. Obj ×40.
Figure 8:
FIG. 8 is a high magnification of the picture of FIG. 7. Eosin counterstaining. Obj ×63 oil.

| Time | Information obtained from the experiments |
|---|---|
|  | See FIG. 7, which is an autoradiogaphic picture of a prostate 48 hours after transurethral injection tritiated testosterone. As can be seen, the cells lining the ducts of the prostatic glands are still heavily labeled. The stromal elements do not show activity. There is minimal activity seen outside the nuclei.<br>See also FIG. 8, which is a high magnification FIG. 7 and clearly shows the nuclear labeling of the glandular ducts, suggesting that the testosterone remains bound to its nuclear AR receptors even 48 hours after the transurethral injection with the catheter. |

TABLE 2

Results of the tritium labeled flutamide

Figure 9:
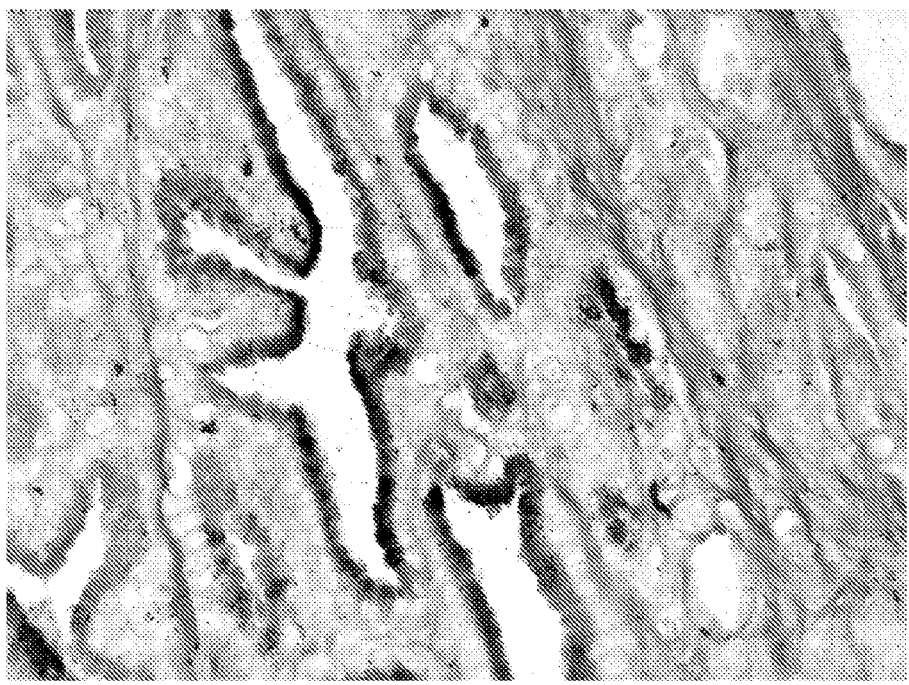
FIG. 9 is an autoradiographic picture of a prostate 1 hour after transurethral injection of 150 uCi tritiated flutamide. Eosin counterstaining. Obj ×40.
Figure 10:
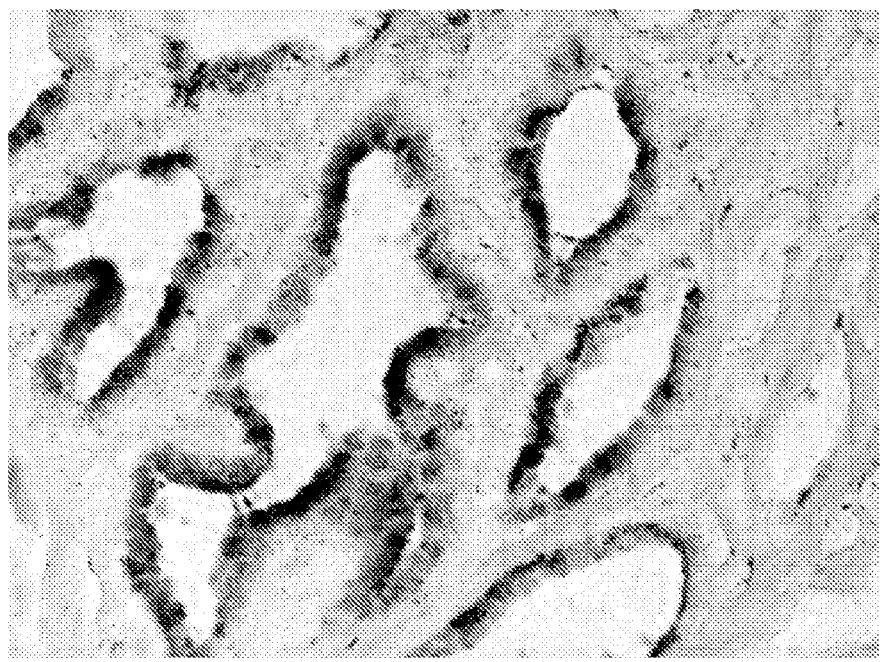
FIG. 10 is an autoradiographic picture of a prostate 6 hours after transurethral injection of 150 uCi tritiated flutamide. Eosin counterstaining. Obj ×40.
Figure 11:
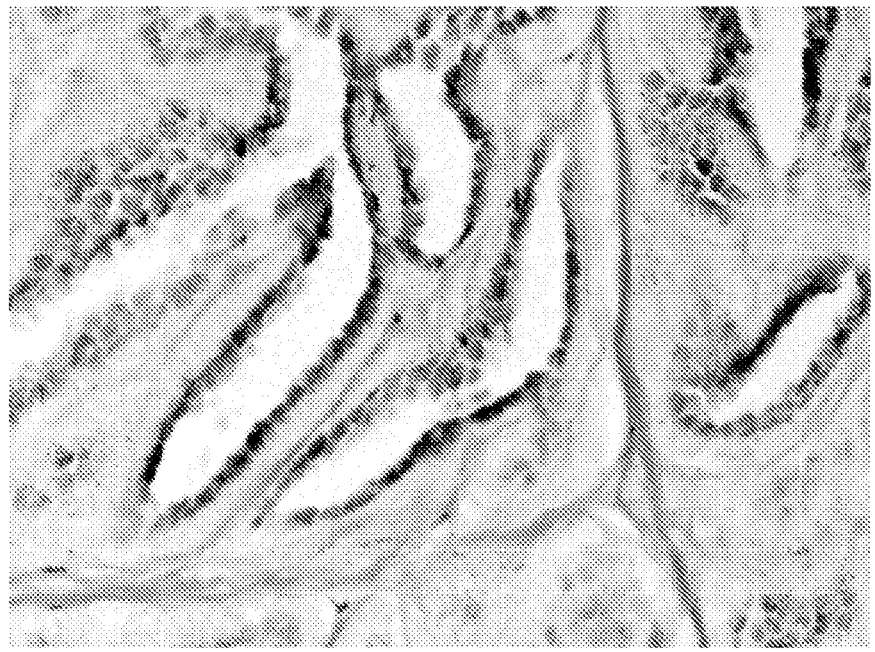
FIG. 11 is an autoradiographic picture of a prostate 12 hours after transurethral injection of 150 uCi tritiated flutamide. Eosin counterstaining. Obj ×40.
Figure 12:
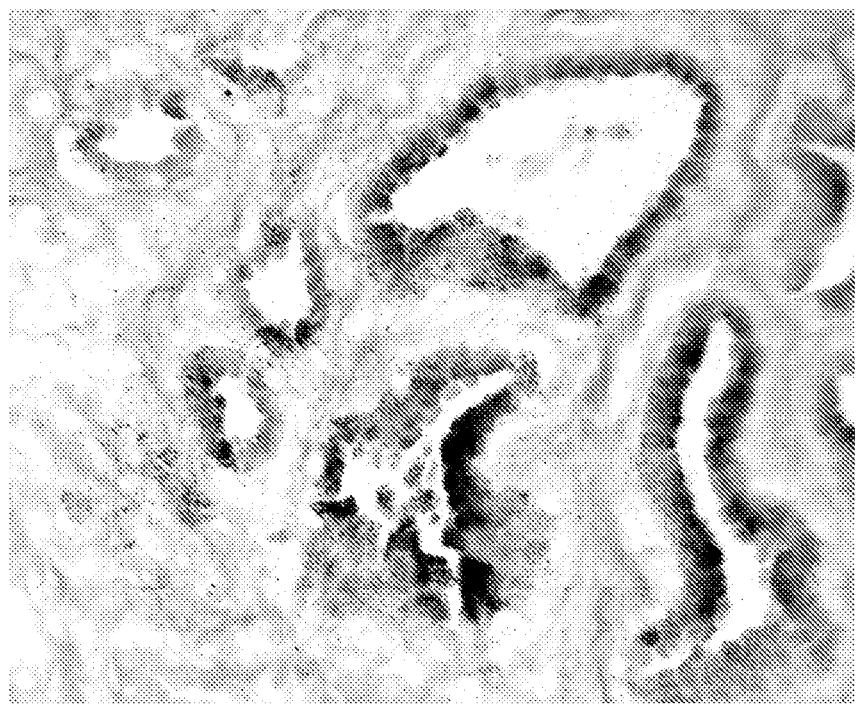
FIG. 12 is an autoradiographic picture of a prostate 24 hours after transurethral injection of 150 uCi tritiated flutamide. Eosin counterstaining. Obj ×40.
Figure 13:
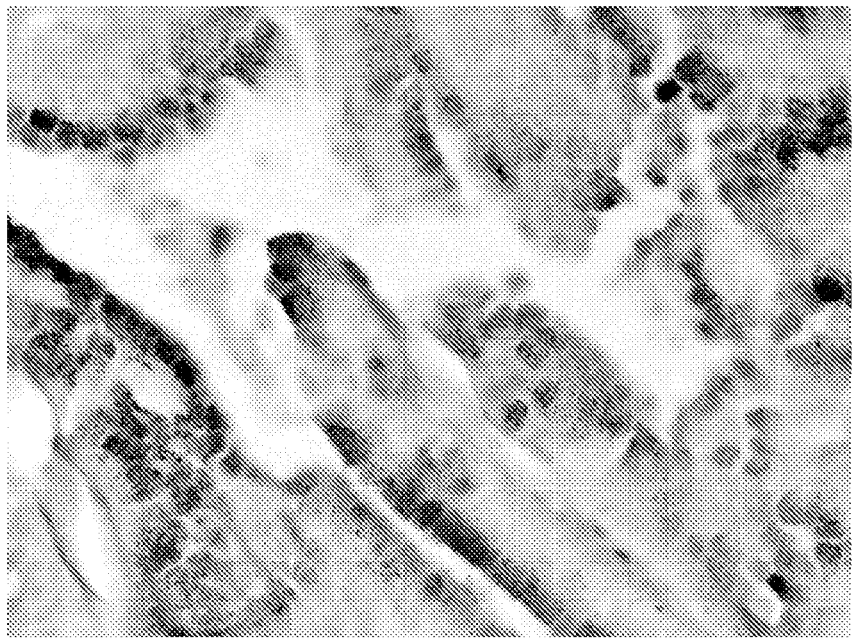
FIG. 13 is an autoradiographic picture of a prostate 48 hours after transurethral injection of 150 uCi tritiated flutamide. Eosin counterstaining. Obj ×40.

| Time | Information obtained from the experiments |
|---|---|
| 1 hour | Strong, diffuse activity scattered over the whole prostate including the stroma. Medium intensity nuclear activity is already present. See FIG. 9, which shows a prostate 1 hour after injection tritiated flutamide. The grains are scattered over all the structures including the stroma, although the activity has already concentrated overwhelmingly over the nuclei of the glands. This suggest that the early travel of the activity is diffuse, includes the stroma, and is not restricted to the glandular ducts. This also suggests that the nuclear receptors avidly bind the AR antagonist, which might decrease the early loss in activity. |
| 6 hours | Strong, selective glandular (but not stromal or muscular) nuclear activity in diffuse distribution over the whole prostate extending from the periurethral area to the periphery of the gland. Practically no free (extra-nuclear) activity. See FIG. 10, which shows the prostate 6 hours after injection tritiated flutamide. A small number of grains are still scattered over all the structures, including the stroma, but the bulk of the activity is concentrated over the nuclei of the prostatic glands. |
| 12 hours | Strong, selective glandular (but not stromal or muscular) nuclear activity in diffuse distribution over the whole prostate from the periurethral area to the periphery of the gland. Practically no extra-nuclear activity. See FIG. 11, which shows a prostate 12 hours after injection tritiated flutamide. Strong accumulation of the grains over the nuclei of the glandular cells. No activity in the stroma. |
| 24 hours | Strong nuclear binding, minimal unbound activity scattered in the gland. See FIG. 12, which shows a prostate 24 hours after injection tritiated flutamide. Strong accumulation of the grains over the nuclei of the glandular cells. No activity in the stroma. Practically the same distribution of the activity as at 12 hours. |
| 48 hours | Still strong, although somewhat less activity over the glandular nuclei; the distribution of the activity still covers the whole prostate, minimal scattered extra-nuclear labeling. See FIG. 13, which shows a prostate 48 hours after injection of tritiated flutamide. Strong accumulation of the grains over the nuclei of the glandular cells. No activity in the stroma. Practically the same distribution of the activity as at 12 and 24 hours. |

Samples from the liver, seminal vesicle, seminal duct, epididymis and testicles are harvested from each isotope treated animal for parallel autoradiography to test for regurgitation into the urogenital organs or escape into the blood stream and distant organs such as the liver.

Figure 14:
FIG. 14 is an autoradiographic picture of the liver from a dog (same as FIG. 13) 48 hours after transurethral injection of 150 uCi tritiated flutamide. Eosin staining. Obj ×10.

FIG. 14 shows an autoradiographic picture of the liver from a dog (same as FIG. 13) 48 hours after transurethral injection of tritiated flutamide. No grains are seen in the liver, although the liver is known to contain an abundance of androgen receptors. (See Tavian D, et al., "Androgen receptor mRNA underexpression in poorly differentiated human hepatocellular carcinoma," *Histol. Histopathol.* 17, 2002 Oct.; 17(4): 1113-9.) This suggests that there is no significant escape into the systemic circulation.

Figure 15:
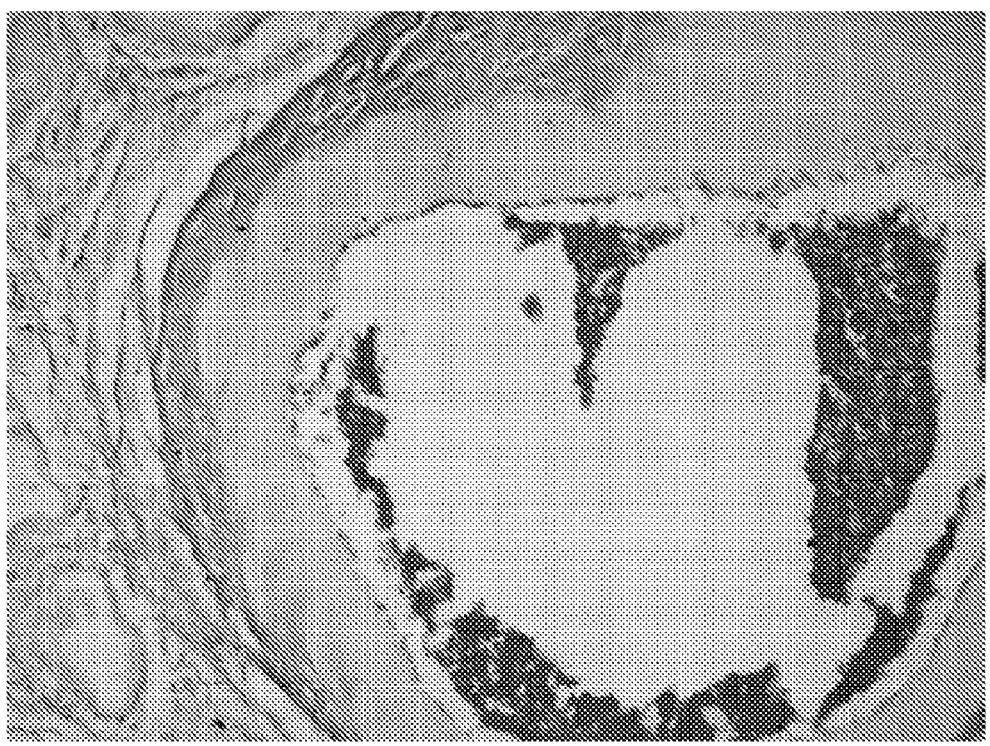
FIG. 15 is an autoradiographic picture of the epididymis of a dog (same as FIG. 10) 6 hours after transurethral injection of 150 uCi tritiated flutamide. Eosin staining. Obj ×10.

FIG. 15 is an autoradiographic picture of the epididymis of a dog (same as FIG. 10) 6 hours after transurethral injection of tritiated flutamide. No grains are seen in the epididymis suggesting that there is no regurgitation of the label at the time of the injection. (Seminal vesicle, seminal duct and testicular samples remained all negative at all time points).

EXAMPLE 2

1 ml of 5 mCi $^{99m}$Tc complexed with hexamethyl-propyleneamine oxime (99mTc HM-PAO) (Ceretec®; Amersham Health, Arlington Heights, Ill., USA) is injected locally into the prostate tissue of elderly dogs (>6-year old) with proven prostatic hyperplasia, as described in Example 1 above.

Figure 16:
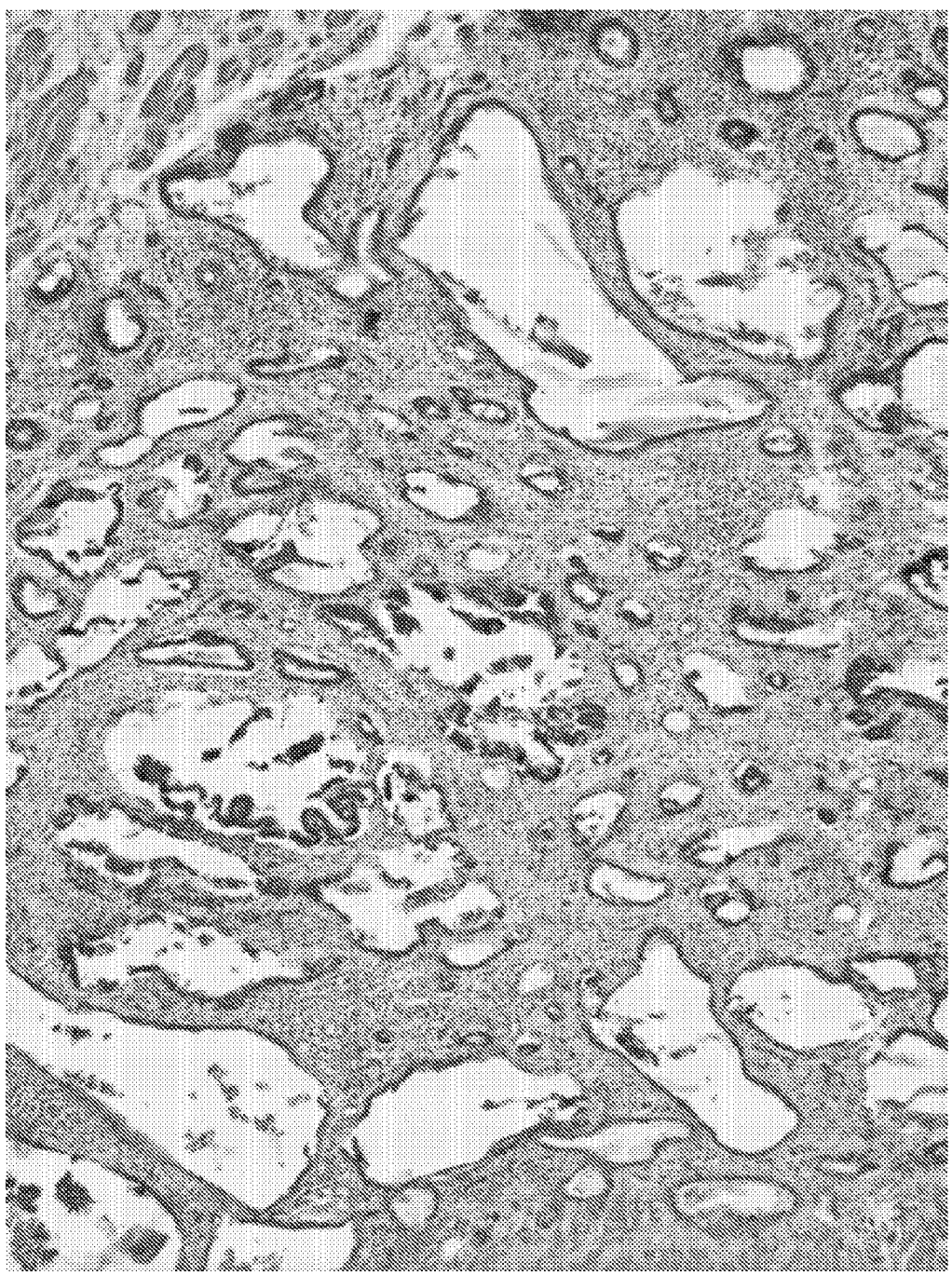
FIG. 16 is a photograph of a paraffin embedded, haematoxylin and eosin (H&E) stained section of a prostate, 4 days after administration of $^{99m}$Tc complexed with hexamethylpropyleneamine oxime. Obj ×5.

The animals are euthanized after 4 days, and the prostates harvested from a suprapubic incision A paraffin embedded, haematoxylin and eosin (H&E) stained section of one dog is illustrated in FIG. 16. The glands seen in the photograph are almost completely destroyed. Although the shrunken contours of the glands are recognizable, the lining glandular cells are missing or are shredded into the lumen (e.g., see the glands in the middle of the photograph). The stroma is infiltrated with inflammatory cells.

Although various embodiments are specifically illustrated and described herein, it will be appreciated that modifications and variations of the present invention are covered by the above teachings and are within the purview of the appended claims without departing from the spirit and intended scope of the present invention. Furthermore, the above examples should not be interpreted to limit the modifications and variations of the present invention covered by the claims but are merely illustrative of possible variations.

The invention claimed is:

1. A method for delivering a therapeutic agent into the prostate gland of a mammalian subject, said method comprising:
    (a) advancing a delivery catheter that comprises a tissue penetrating member through the urethra of said subject until said tissue penetrating member is positioned in the prostatic segment of the urethra, wherein said catheter comprises a shaft and an working member that comprises an expanding member which expands to engage the urethral wall in the prostatic segment of the urethra and a tissue penetrating member that is not a needle, wherein said working member is adapted to extend the tissue penetrating member through the urethral wall;
    (b) extending said tissue penetrating member through the urethral wall upon expansion of the expanding member;
    (c) injecting the therapeutic agent into tissue of the prostate gland via the tissue penetrating member; and
    (d) removing said catheter from the subject.

2. The method of claim 1, wherein said delivery catheter comprises a plurality of said tissue penetrating members.

3. The method of claim 1, wherein said injected therapeutic agent is in the form of a fluid.

4. The method of claim 3, wherein said fluid comprises a liquid.

5. The method of claim 4, further comprising estimating the volume of the prostate, wherein a volume of said fluid that is equal to 5-35% of the estimated prostate volume is injected.

6. The method of claim 5, wherein said volume of the prostate is measured using ultrasonography.

7. The method of claim 3, wherein said fluid comprises a gas.

8. The method of claim 1, wherein said therapeutic agent is delivered into a subject diagnosed with benign prostate hypertrophy.

9. The method of claim 1, wherein said therapeutic agent is delivered into a subject diagnosed with prostate cancer.

10. The method of claim 1, wherein said therapeutic agent is delivered into a subject diagnosed with a prostatic infection.

11. The method of claim 1, wherein steps (a) to (d) are repeated.

12. The method of claim 1, wherein said catheter is positioned with image guidance.

13. The method of claim 12, wherein said image guidance comprises ultrasonography.

14. The method of claim 12, wherein said image guidance comprises fluoroscopy.

15. The method of claim 12, wherein said image guidance comprises both ultrasonography and fluoroscopy.

16. The method of claim 12, wherein said catheter is provided with positioning markers to aid said image guidance.

17. The method of claim 1, wherein said catheter further comprises a positioning balloon that is distal to said penetrating member, and wherein said positioning balloon is inflated in the bladder of the subject.

18. The method of claim 1, wherein injection of said therapeutic agent is assisted using electrophoresis or electroporation.

19. The method of claim 1, wherein said penetrating member has a penetration depth between 0.25 and 25 mm.

20. The method of claim 1, wherein said expanding member is a balloon.

21. The method of claim 20, wherein said tissue penetrating member is disposed on or within a surface of said balloon and wherein said tissue penetrating members are forced through the urethral wall and into prostatic tissue upon inflation of the balloon.

22. The method of claim 21, wherein a plurality of tissue penetrating members are disposed on or within a surface of said balloon.

23. The method of claim 21, wherein said penetrating members have a penetration depth between 0.25 and 25 mm.

24. The method of claim 21, wherein said balloon is inflated to between 0.5 and 10 atmospheres.

25. The method of claim 21, wherein said balloon relieves urethral stricture in said subject upon inflation.

26. The method of claim 1, wherein said shaft further comprises a guide wire lumen.

27. The method of claim 26, wherein said therapeutic agent is selected from agents that selectively target prostatic epithelial cell production or apoptosis, agents that selectively target testosterone-DHT conversion levels within the prostate, agents that affect androgen receptor binding within the prostate, and cell-cycle inhibitors.

28. The method of claim 1, wherein said shaft comprises a urine lumen, a drug delivery lumen, and a balloon inflation lumen.

29. The method of claim 1, wherein said tissue penetrating member is a nipple.

30. The method of claim 1, wherein said delivery catheter comprises a plurality of nipples as tissue penetrating members.

* * * * *